US008641754B2

(12) United States Patent
Boyle et al.

(10) Patent No.: US 8,641,754 B2
(45) Date of Patent: Feb. 4, 2014

(54) ENDOLUMINAL STENT, SELF-SUPPORTING ENDOLUMINAL GRAFT AND METHODS OF MAKING SAME

(75) Inventors: Christopher T. Boyle, San Antonio, TX (US); Steven R. Bailey, San Antonio, TX (US); Julio C. Palmaz, San Antonio, TX (US); Christopher E. Banas, San Antonio, TX (US)

(73) Assignee: Advanced Bio Prosthetic Surfaces, Ltd. a wholly owned subsidiary of Palmaz Scientific, Inc., Dallas, TX (US)

(*) Notice: Subject to any disclaimer, the term of this patent is extended or adjusted under 35 U.S.C. 154(b) by 1854 days.

(21) Appl. No.: 11/327,795

(22) Filed: Jan. 6, 2006

(65) Prior Publication Data

US 2006/0116751 A1    Jun. 1, 2006

Related U.S. Application Data

(62) Division of application No. 09/707,685, filed on Nov. 7, 2000, and a division of application No. 10/120,800, filed on Apr. 11, 2002, now abandoned.

(51) Int. Cl.
*A61F 2/82* (2013.01)

(52) U.S. Cl.
USPC .......................................... 623/1.15

(58) Field of Classification Search
USPC ................................ 623/1.13–1.22
See application file for complete search history.

(56) References Cited

U.S. PATENT DOCUMENTS 4,510,182 A   4/1985  Cornils et al. ................. 427/162

4,665,906 A   5/1987  Jervis ............................. 128/92

(Continued)

FOREIGN PATENT DOCUMENTS

| DE | 1452370 | 3/1974 | ............... C21C 37/15 |
| DE | 199 37 638 | 5/2001 | ................ A61F 2/04 |

(Continued)

OTHER PUBLICATIONS

"Liquid Sources for Chemical Vapor Deposition of Group 6 Metals and Metal Nitrides" by Gordon, et al., www.techtransfer.harvard.edu/cgi-bin/TALSearch.cgi?full_report=1&case=3, Case No. 1709.

(Continued)

*Primary Examiner* — Thomas J Sweet
*Assistant Examiner* — Cheryl Miller
(74) *Attorney, Agent, or Firm* — David G. Rosenbaum; J. Peter Paredes; Rosenbaum IP

(57) ABSTRACT

An endoluminal stent composed of a plurality of first structural elements arrayed to form the circumference of the stent and extending along the longitudinal axis of the stent, and a plurality of second structural elements that interconnect adjacent pairs of first structural elements. The plurality of first structural elements have either a linear shape or a generally sinusoidal configuration with either a regular or irregular periodicity or regions of regular and regions of irregular periodicity between the peaks and troughs of the pattern, with the peaks and troughs projecting from the first structural elements in the circumferential axis. The plurality of second structural elements are generally linear or sinusoidal-shaped members which interconnect an apex of a peak of one of the plurality of first structural elements with an apex of a valley of a second and adjacent one of the plurality of first structural elements. Each of the plurality of second structural elements are generally oriented parallel to the circumferential axis of the stent.

12 Claims, 11 Drawing Sheets

(56) References Cited

U.S. PATENT DOCUMENTS

| | | | | |
|---|---|---|---|---|
| 4,751,099 A | 6/1988 | Niino et al. | | 427/34 |
| 4,776,337 A | 10/1988 | Palmaz | | 128/343 |
| 4,846,834 A | 7/1989 | von Recum et al. | | 623/11 |
| 5,049,251 A | 9/1991 | Inone | | 204/192 |
| 5,061,914 A | 10/1991 | Busch et al. | | 337/140 |
| 5,084,151 A | 1/1992 | Vallana | | 204/192.11 |
| 5,133,845 A | 7/1992 | Vallana et al. | | 204/192 |
| 5,190,546 A | 3/1993 | Jervis | | 606/78 |
| 5,242,710 A | 9/1993 | Claar et al. | | 427/248 |
| 5,277,933 A | 1/1994 | Claar et al. | | 427/248 |
| 5,358,615 A | 10/1994 | Grant et al. | | 204/192.15 |
| 5,370,684 A | 12/1994 | Vallana et al. | | 623/1 |
| 5,387,247 A | 2/1995 | Vallana et al. | | 623/2 |
| 5,421,955 A | 6/1995 | Lau et al. | | 216/48 |
| 5,477,864 A | 12/1995 | Davidson | | 128/771 |
| 5,482,574 A | 1/1996 | Goldstein | | 148/517 |
| 5,508,116 A | 4/1996 | Barrett | | 428/567 |
| 5,514,154 A | 5/1996 | Lau et al. | | 606/195 |
| 5,540,820 A | 7/1996 | Terakado et al. | | 204/192.3 |
| 5,545,210 A | 8/1996 | Hess et al. | | 623/1 |
| 5,569,295 A | 10/1996 | Lam | | 606/198 |
| 5,578,149 A | 11/1996 | DeScheerder | | 148/563 |
| 5,593,442 A | 1/1997 | Klein | | 623/12 |
| 5,597,378 A | 1/1997 | Jervis | | 606/78 |
| 5,597,458 A | 1/1997 | Sanchez, Jr. | | 204/192.3 |
| 5,603,721 A | 2/1997 | Lau et al. | | 606/195 |
| 5,605,714 A | 2/1997 | Dearnaley et al. | | 427/2.24 |
| 5,607,445 A | 3/1997 | Summers | | 606/198 |
| 5,607,463 A | 3/1997 | Schwartz et al. | | 623/1 |
| 5,609,629 A | 3/1997 | Fearnot et al. | | 623/1 |
| 5,624,508 A | 4/1997 | Flomenblit et al. | | 148/510 |
| 5,628,788 A | 5/1997 | Pinchuk | | 623/1 |
| 5,630,840 A | 5/1997 | Mayer | | 623/1 |
| 5,635,144 A | 6/1997 | Akluft | | 422/186.05 |
| 5,647,858 A | 7/1997 | Davidson | | 604/264 |
| 5,656,036 A | 8/1997 | Palmaz | | 623/12 |
| 5,683,453 A | 11/1997 | Palmaz | | 623/1 |
| 5,685,961 A | 11/1997 | Pourrezaei et al. | | 204/192 |
| 5,690,670 A | 11/1997 | Davidson | | 606/198 |
| 5,723,219 A | 3/1998 | Kolluri | | 428/411.1 |
| 5,725,573 A | 3/1998 | Dearnaley et al. | | 623/2 |
| 5,728,150 A | 3/1998 | McDonald et al. | | 623/1 |
| 5,728,158 A | 3/1998 | Lau et al. | | 623/12 |
| 5,733,303 A | 3/1998 | Israel et al. | | 606/198 |
| 5,735,896 A | 4/1998 | Amon et al. | | 623/11 |
| 5,744,515 A | 4/1998 | Clapper | | 523/113 |
| 5,765,418 A | 6/1998 | Rosenberg | | 72/47 |
| 5,772,864 A | 6/1998 | Moller et al. | | 205/73 |
| 5,776,161 A | 7/1998 | Globerman | | 606/194 |
| 5,780,807 A | 7/1998 | Saunders | | 219/121 |
| 5,782,908 A | 7/1998 | Cahalan et al. | | 623/1 |
| 5,782,910 A | 7/1998 | Davidson | | 623/3 |
| 5,788,558 A | 8/1998 | Klein | | 451/136 |
| 5,810,872 A * | 9/1998 | Kanesaka et al. | | 623/1.15 |
| 5,811,151 A | 9/1998 | Hendricks et al. | | 427/2.24 |
| 5,824,045 A | 10/1998 | Alt | | 623/1 |
| 5,824,049 A | 10/1998 | Ragheb | | 623/1 |
| 5,824,056 A | 10/1998 | Rosenberg | | 623/1 |
| 5,840,009 A | 11/1998 | Fischell et al. | | 600/3 |
| 5,843,117 A | 12/1998 | Alt et al. | | 606/194 |
| 5,843,120 A | 12/1998 | Israel et al. | | 606/198 |
| 5,843,289 A | 12/1998 | Lee et al. | | 204/192 |
| 5,849,206 A | 12/1998 | Amon et al. | | 216/63 |
| 5,853,419 A | 12/1998 | Imran | | 606/191 |
| 5,855,600 A | 1/1999 | Alt | | 623/1 |
| 5,855,802 A | 1/1999 | Acciai et al. | | 216/8 |
| 5,855,955 A | 1/1999 | Claar et al. | | 427/248.1 |
| 5,858,556 A | 1/1999 | Eckert et al. | | 428/586 |
| 5,866,113 A | 2/1999 | Hendricks et al. | | 424/78.17 |
| 5,868,782 A | 2/1999 | Frantzen | | 606/198 |
| 5,873,904 A | 2/1999 | Ragheb et al. | | 623/1 |
| 5,876,432 A | 3/1999 | Lau et al. | | 623/1 |
| 5,879,370 A | 3/1999 | Fischell et al. | | 606/198 |
| 5,891,507 A | 4/1999 | Jayaraman | | 427/2.25 |
| 5,895,406 A | 4/1999 | Gray et al. | | 606/198 |
| 5,899,935 A | 5/1999 | Ding | | 623/1 |
| 5,907,893 A | 6/1999 | Zadno-Azizi | | 29/6.1 |
| 5,913,896 A | 6/1999 | Boyle et al. | | 623/1 |
| 5,919,225 A | 7/1999 | Lau et al. | | 623/1 |
| 5,925,063 A | 7/1999 | Khosravi | | 606/200 |
| 5,932,036 A | 8/1999 | Fukai | | 148/670 |
| 5,932,299 A | 8/1999 | Katoot | | 427/508 |
| 5,938,682 A | 8/1999 | Hojeibane et al. | | 606/198 |
| 5,938,697 A | 8/1999 | Killion et al. | | 623/1 |
| 5,945,153 A | 8/1999 | Dearnaley | | 427/2.12 |
| 5,951,881 A | 9/1999 | Rogers et al. | | 216/41 |
| 5,954,724 A | 9/1999 | Davidson | | 606/76 |
| 5,955,588 A | 9/1999 | Tsang et al. | | 536/21 |
| 5,962,138 A | 10/1999 | Kolluri et al. | | 428/411.1 |
| 5,968,091 A | 10/1999 | Pinchuk et al. | | 623/1 |
| 5,972,018 A | 10/1999 | Israel et al. | | 606/198 |
| 5,972,027 A | 10/1999 | Johnson | | 623/1 |
| 5,984,905 A | 11/1999 | Dearnaley et al. | | 604/265 |
| 6,007,573 A | 12/1999 | Wallace et al. | | 623/1 |
| 6,015,429 A | 1/2000 | Lau et al. | | 623/1 |
| 6,016,693 A | 1/2000 | Viani et al. | | 73/105 |
| 6,019,784 A | 2/2000 | Hines | | 623/1 |
| 6,022,370 A | 2/2000 | Tower | | 606/194 |
| 6,027,526 A | 2/2000 | Limon et al. | | 623/1 |
| 6,033,433 A | 3/2000 | Ehr et al. | | 623/1 |
| 6,042,597 A | 3/2000 | Kveen et al. | | 606/198 |
| 6,056,776 A | 5/2000 | Lau et al. | | 623/1 |
| 6,059,808 A | 5/2000 | Boussignac | | 606/191 |
| 6,059,822 A * | 5/2000 | Kanesaka et al. | | 623/1.15 |
| 6,066,167 A | 5/2000 | Lau et al. | | 623/1 |
| 6,066,168 A | 5/2000 | Lau et al. | | 623/1 |
| 6,066,169 A | 5/2000 | McGuiness | | 623/1.16 |
| 6,071,305 A | 6/2000 | Brown et al. | | 623/1 |
| 6,086,773 A | 7/2000 | Dufresne et al. | | 216/8 |
| 6,096,175 A | 8/2000 | Roth | | 204/192 |
| 6,103,320 A | 8/2000 | Matsumoto et al. | | 427/535 |
| 6,106,642 A | 8/2000 | DiCarlo et al. | | 148/563 |
| 6,113,705 A | 9/2000 | Ohashi et al. | | 118/730 |
| 6,113,982 A | 9/2000 | Claar et al. | | 427/248.1 |
| 6,120,536 A | 9/2000 | Ding et al. | | 623/1.43 |
| 6,120,847 A | 9/2000 | Yang et al. | | 427/335 |
| 6,126,761 A | 10/2000 | DeHaven et al. | | 148/518 |
| 6,126,793 A | 10/2000 | Sugiyama et al. | | 204/192.23 |
| 6,136,159 A | 10/2000 | Buckfeller et al. | | 204/192.12 |
| 6,149,742 A | 11/2000 | Carpenter et al. | | 148/563 |
| H1924 H | 12/2000 | Zabinski et al. | | 204/192.16 |
| 6,156,052 A | 12/2000 | Richter et al. | | 606/191 |
| 6,156,373 A | 12/2000 | Zhong et al. | | |
| 6,173,672 B1 | 1/2001 | Shepard, Jr. | | 118/723 |
| 6,190,404 B1 | 2/2001 | Palmaz et al. | | 623/1.15 |
| 6,190,407 B1 | 2/2001 | Ogle et al. | | 623/1.51 |
| 6,194,088 B1 | 2/2001 | Yoshida et al. | | 428/660 |
| 6,202,304 B1 | 3/2001 | Shatz | | 29/896.6 |
| 6,203,505 B1 | 3/2001 | Jalisi et al. | | 600/585 |
| 6,206,911 B1 | 3/2001 | Milo | | 623/1.15 |
| 6,207,536 B1 | 3/2001 | Matsumoto et al. | | 438/478 |
| 6,217,952 B1 | 4/2001 | Sugiyama et al. | | 427/577 |
| 6,231,923 B1 | 5/2001 | Teverovsky et al. | | 427/248.1 |
| 6,238,491 B1 | 5/2001 | Davidson et al. | | 148/237 |
| 6,245,104 B1 | 6/2001 | Alt | | 623/1.46 |
| 6,248,401 B1 | 6/2001 | Chiang et al. | | 427/255.7 |
| 6,253,441 B1 | 7/2001 | Wheat et al. | | 29/527.2 |
| 6,258,121 B1 | 7/2001 | Yang et al. | | 623/1.46 |
| 6,258,182 B1 | 7/2001 | Schetky et al. | | 148/402 |
| 6,258,417 B1 | 7/2001 | Goswami et al. | | 427/452 |
| 6,261,320 B1 | 7/2001 | Tam et al. | | 623/1.15 |
| 6,264,595 B1 | 7/2001 | Delfino et al. | | 60/1 |
| 6,264,598 B1 | 7/2001 | Armini | | 600/3 |
| 6,264,685 B1 | 7/2001 | Ahari | | 623/1.15 |
| 6,264,687 B1 | 7/2001 | Tomonto | | 623/1.16 |
| 6,267,782 B1 | 7/2001 | Ogle et al. | | 623/1.1 |
| 6,267,867 B1 | 7/2001 | Olson | | 205/640 |
| 6,274,014 B1 | 8/2001 | Matsumoto et al. | | 204/298.11 |
| 6,284,316 B1 | 9/2001 | Sandhu et al. | | 427/255.391 |
| 6,287,277 B1 | 9/2001 | Yan | | 604/96.01 |
| 6,287,430 B1 | 9/2001 | Matsumoto et al. | | 204/192.26 |
| 6,290,720 B1 | 9/2001 | Khosravi et al. | | 623/1.13 |
| 6,293,966 B1 | 9/2001 | Frantzen | | 623/1.15 |
| 6,299,604 B1 | 10/2001 | Ragheb et al. | | 604/265 |

(56) References Cited

U.S. PATENT DOCUMENTS

| | | | |
|---|---|---|---|
| 6,299,755 B1 | 10/2001 | Richter | 205/651 |
| 6,306,141 B1 | 10/2001 | Jervis | 606/78 |
| 6,306,276 B1 | 10/2001 | Nobe et al. | 205/238 |
| 6,309,414 B1 | 10/2001 | Rolando et al. | 623/1.15 |
| 6,312,456 B1 | 11/2001 | Kranz et al. | 623/1.13 |
| 6,312,463 B1 | 11/2001 | Rourke et al. | 623/1.39 |
| 6,315,794 B1 | 11/2001 | Richter | 623/134 |
| 6,327,772 B1 | 12/2001 | Zadno-Azizi | 29/557 |
| 6,409,754 B1 * | 6/2002 | Smith et al. | 623/1.16 |
| 6,475,236 B1 * | 11/2002 | Roubin et al. | 623/1.15 |
| 2001/0000043 A1 | 3/2001 | Israel et al. | 606/198 |
| 2001/0003146 A1 | 6/2001 | Jalisi et al. | 600/585 |
| 2001/0009169 A1 | 7/2001 | Kajiwara et al. | 148/563 |
| 2001/0009220 A1 | 7/2001 | Mizuno et al. | 427/569 |
| 2001/0011158 A1 | 8/2001 | Howland | 600/585 |
| 2001/0021570 A1 | 9/2001 | Lin et al. | 438/455 |
| 2001/0032013 A1 | 10/2001 | Marton | 623/1.15 |
| 2001/0037146 A1 | 11/2001 | Lau et al. | 623/1.16 |
| 2001/0037147 A1 | 11/2001 | Lau et al. | 623/1.16 |
| 2001/0039449 A1 | 11/2001 | Johnson et al. | 623/1.19 |
| 2001/0047200 A1 * | 11/2001 | White et al. | 623/1.15 |
| 2001/0047201 A1 | 11/2001 | Cox et al. | 623/1.16 |
| 2001/0055647 A1 | 12/2001 | Tamura et al. | 427/177 |
| 2001/0055654 A1 | 12/2001 | Halpern | 427/600 |
| 2002/0042649 A1 | 4/2002 | Schaldach et al. | 623/1.15 |
| 2002/0165600 A1 | 11/2002 | Banas et al. | 623/1.11 |
| 2003/0018381 A1 * | 1/2003 | Whitcher et al. | 623/1.15 |

FOREIGN PATENT DOCUMENTS

| | | | |
|---|---|---|---|
| EP | 0 400 947 | 12/1990 | C23C 16/26 |
| EP | 0 442 303 | 8/1991 | C23C 16/26 |
| FR | 2 777 771 | 10/1999 | A61F 2/06 |
| JP | 51055724 | 5/1976 | A61C 13/00 |
| JP | 10072319 | 10/1999 | B01D 59/34 |
| RU | 2110606 | 5/1998 | C23C 14/34 |
| WO | 97/07257 | 2/1997 | C23C 14/00 |
| WO | 97/44692 | 11/1997 | G02B 6/16 |
| WO | 98/13537 | 4/1998 | C25D 1/00 |
| WO | 98/45506 | 10/1998 | C25D 7/04 |
| WO | 99/16385 | 4/1999 | A61F 2/06 |
| WO | 99/23977 | 5/1999 | A61F 2/06 |
| WO | 99/62432 | 12/1999 | A61F 2/06 |
| WO | 00/54704 | 9/2000 | A61F 2/06 |
| WO | 00/55181 | 9/2000 | C07K 1/00 |
| WO | WO01/35865 | 5/2001 | A61F 2/06 |
| WO | 01/53559 | 7/2001 | C23C 14/14 |
| WO | 01/55473 | 8/2001 | C23C 14/00 |
| WO | 01/56502 | 8/2001 | A61F 2/06 |
| WO | 01/85064 | 11/2001 | A61F 2/06 |
| WO | 01/91918 | 12/2001 | B05C 5/02 |

OTHER PUBLICATIONS

"Fabrication of Small-Scale Coils and Bands as Photomasks on Optical Fibers for Generation of In-Fiber Gratings, Electromagnets as Micro-NMR Coils, Microtransformers, and Intra-Vascular Stents" www.techtransfer.harvard.edu/cgi-bin/TALSearch.cgi?full_report=1&case=72, Case No. 1263.
"Reactions of Biological Cells to Nanostructures", by Curtis, et al., AVS 46th International Symposium, Paper BI-WeM2 (Oct. 27, 1999).
"Biocompatibility of Cardiac Cells on Silane-Modified Surfaces" AVS 46th International Symposium, Paper BI-WeM5 (Oct. 27, 1999).
"Biofunctionalization of Surfaces with Peptide Amphilphiles" AVS 46th International Symposium, Paper No. BI-WeM7 (Oct. 27, 1999).
"Plasma Copolymer Surfaces for Cell Culture" AVS 46th International Symposium, Paper No. Paper BI-WeM9 (Oct. 27, 1999).
"Plasma Co-polymer Surfaces for the Controlled Adsorption of Common Proteins" AVS 46th International Symposium, Paper No. BI-FrM2 (Oct. 29, 1999).
"Biofilm—Titanium Chemistry of Adhesion Using X-ray Photoelectron Spectroscopy" AVS 46th International Symposium, Paper No. BI-FrM10.
"Nanoscale Patterning of Gold for Attachment of Supported Lipid Bilayers" AVS 46th International Symposium, Paper No. BI-FrM10.
"Focused Ion Beam NonaFabrication", http://www.glue.umd.edu/~astan/avs04.htm.
"Amorphous Carbon and C:N Thin Films" http://www.glue.umd.edu/~astan/avs01.htm.
Multilayer Ceramic/Metallic Coatings by Ion Beam-Assisted, Electron Beam Physical Vapor (EB-PVD) Deposition, Penn State Appled Research Laboratory, pp. 1-4 (1997).
"Benefits From Diamond-Like Coated Stainless Steel Stents", http://www.phytis.com/stents0.htm, pp. 1-2.
"Adhesion of Bovine Serus Albumin on Coated DLC (Diamond-Like) and Uncoated ($SiO_2$ / $TiO_2$) Sensor Chips", http://www.phytis.com/stent4.htm, pp. 1-2.
"Flow Cytometric Investigation", http://www.phytis.com/stent6.htm, pp. 1-3.
"Pre-clinical and Clinical Evaluation", http://www.phytis.com/stent2.htm, pp. 1-2.
"The New Phytis Stent", http://www.phytis.com/stent1.htm, pp. 1-2.
"Invulnerability and Resistance of DLC-Coating", http://www.phytis.com/stent3.htm, pp. 1-3.
"Material in Use and Its Biocompatibility", http://www.phytis.com/stent5.htm, pp. 1-2.
"Expertise Concerning the Implementation of the Phytis Diamond as Stent Performed at the Institute for Experimental Medicine (IEM)", http://www.phytis.com/stent9.htm, pp. 1.
"Phytis L.D.A. Home Page information", http://www.phytis.com/content/htm, pp. 1-15.
"Risk Analysis of Stents With a Diamond-Like Coated Surface for Use in Prosthetic Implants", http://www.phytis.com/risk.htm, pp. 1-6.
"Directions for Use, Diamond AS® Stent", http://www.phytis.com/direcuse.htm, pp. 1-8.
"Stents: Literature", http://www.phytis.com/liter.htm, pp. 1-8.
"Vacuum Conditions for Sputtering Thin Film TiNi", *Journal of Vacuum Science and Technology, JVST A Online*, pp. 1-2 (Abstract view).
"Oriented nickel-tetanium shape memory alloy films prepared by annealing during deposition", by Kathleen Gisser, et al., *Applied Physics Letters*, vol. 61, Issue 14, pp. 1632-1634 (Abstract view).
"Relative importance of bombardment energy and intensity in ion plating", K.S. Fancey, et al., *Journal of Vacuum Science & Technology A: Vacuum, Surfaces and Films*, vol. 13, Issue 2, pp. 428-435 (Abstract view) Mar. 1995.
"Role of Bio-Physiochemical Parameters in Cell Adhesion and Rolling-Simulation Analysis" by A. Alshorman, T. David and P. Walker, *BED*, vol. 50, pp. 209-210 (2001).
"Microstructure of Ti-Rich TiNi Thin Films" by A. Ishida, et al., *Proceedings of the Second International Conference on Shape Memory and Superelastic Technologies Asilomar Conference Center*, Pacific Grove, California, USA, pp. 161-166 (1997).
"Thin Film Shape Memory Microvalves with Adjustable Operation Temperature" by M. Kohl, D. Kittmann, E. Quandt, and B. Winzek, *Sensors and Actuators*, vol. 83, pp. 214-219 (2000).
"A Temperature-Controlling Device for Refrigerators" by M.C. Shin, K.K. Jee and B.C. Ku, *Proceedings of the First International Conference on Shape Memory and Superelastic Technologies*, pp. 305-310 (1994).
"Multicomponent Film Deposition by Target Biasing", *IBM Technical Disclosure Bulletin*, pp. 1-2 (Jul. 1980).
"Applications of Shape-Memory Alloy Thin Films" by A.D. Johnson and V.V. Martynov, *Proceedings of the Second International Conference on Shape Memory and Superelastic Technologies Asilomar Conference Center*, Pacific Grove, California, USA, pp. 1-8 (1997).
"Sputter-deposition of TiNi, TiNiPd and TiPd films displaying the two-way shape-memory effect" by E. Quandt, et al., *Sensors and Actuators*, A 53, pp. 434-439 (1996).
"Thin-film Processing of TiNi Shape Memory Alloy" by J.A. Waker and K.J. Gabriel, *Sensors and Actuators*, A21-A23, pp. 243-246 (1990).
"Shape Memory Properties in NiTi Sputter-deposited Film", by J.D. Busch and A.D. Johnson, *J Appl. Phys*, vol. 68, No. 12, pp. 6224-6226 (Dec. 15, 1990).

(56) References Cited

OTHER PUBLICATIONS

"Recent Progress in the Application of Thin Film Shape Memory Alloys" by A.D. Johnson and J.D. Busch, *Proceedings of the First International Conference on Shape Memory and Superelastic Technologies Asilomar Conference Center*, Pacific Grove, California, USA, pp. 299-310 (1994).

"Anomalous Plastic and Elastic Behaviors of Sputter-deposited TiN with 10 or 20 Inserted Thin Al Layers Evaluated by Nanoindentation" by E. Kusano, et al., AVS $47^{th}$ International Symposium, Paper No. TF-TuA3 (Oct. 3, 2000).

"The Nanomechanical Properties of Thin Films" by J.E. Houston, AVS $47^{th}$ International Symposium, Paper No. TF-TuA1 (Oct. 3, 2000).

"Endothelial Cell Organization on Micropatterned Protein Surfaces" by R. Daw, et al., AVS $47^{th}$ International Symposium, Paper No. BI-WeP21 (Oct. 4, 2000).

"Tissue Formation of Hepatocytes on Micro-Porous Films of Polylactide" by T. Nishikawa, et al., AVS $47^{th}$ International Symposium, Paper No. BI+EL-TuA10 (Oct. 3, 2000).

"Cell Response to Chemically and Topographically Modified Surfaces" by D.S. Sutherland, et al., AVS $47^{th}$ International Symposium, Paper No. BI+EL-TuA3 (Oct. 3, 2000).

"Model Surfaces for Studying and Controlling the Adhesion of Cells" M. Mrksich, AVS $47^{th}$ International Symposium, Invited Paper No. BI+EL-TuA1 (Oct. 3, 2000).

"A Concise History of Vacuum Coating Technology, Part 2: 1940 to 1975" by D. Mattox, www.svc.org/HistorvofVac2.html, pp. 1-15.

"Sputtering Targets High-Quality Thin Film Materials" by Ametek Specialty Metal Products online at www.ametek84.com/fd-sputtering.html, pp. 1-3.

"The influence of ion irradiation during film growth on the chemical stability of film/substrate systems" by W. Ensinger, *Surface and Coatings Technology*, vol. 80, pp. 35-48 (1996).

"Progress in Thin Film Shape Memory Microactuators" by Johnson, et al., www.sma-mems.com/recent.htm (Overview), pp. 1-5.

"Thin Film Shape Memory Alloy Microactuators" by TiNi Alloy Company (online).

"The Characteristics of NiTi HCD-Deposited SMA Films" by H. Weixin, et al., *Proceedings of the Second International Conference on Shape Memory and Superelastic Technologies Asilomar Conference Center*, Pacific Grove, California, USA, pp. 167-172 (1997).

"The Effect of HCD Technological Factors on the NiTi SMA Film Thickness" by Q. Pingshan, et al., *Proceedings of the Second International Conference on Shape Memory and Superelastic Technologies Asilomar Conference Center*, Pacific Grove, California, USA, pp. 173-176 (1997).

"Constitutive Parts of a Shape Memory Alloy Titanium Nickel Thin Film Catheter" by L. Buchaillot, et al., *Proceedings of the Second International Conference on Shape Memory and Superelastic Technologies Asilomar Conference Center*, Pacific Grove, California, USA, pp. 183-188 (1997).

"The Effects of Ion Irradiation on NiTi Shape Memory Alloy Thin Films" by F. Goldberg and E. Knystautas, *Proceedings of the Second International Conference on Shape Memory and Superelastic Technologies Asilomar Conference Center*, Pacific Grove, California, USA, pp. 177-182 (1997).

\* cited by examiner

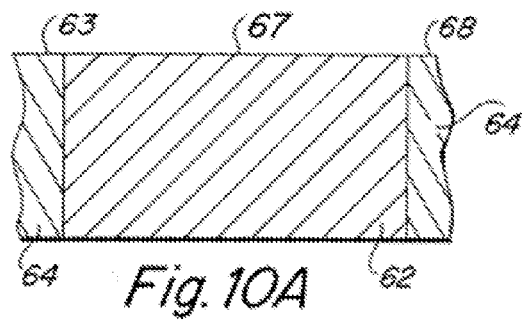
Fig. 10A
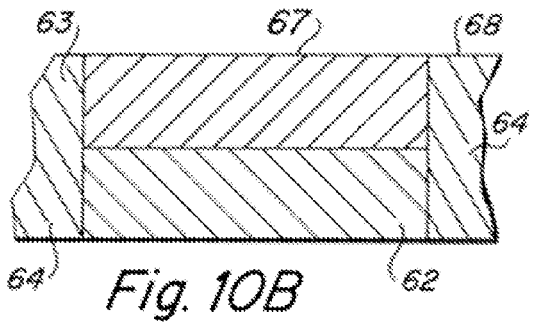
Fig. 10B
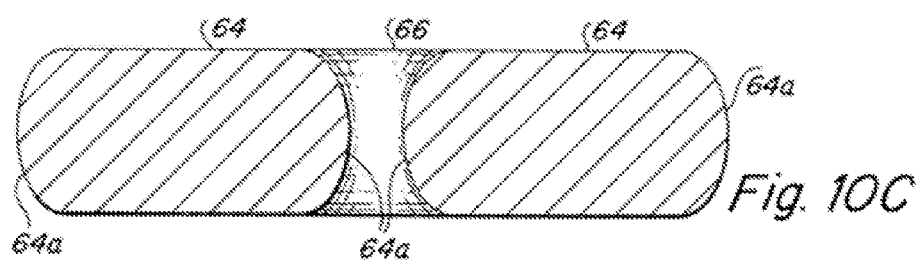
Fig. 10C
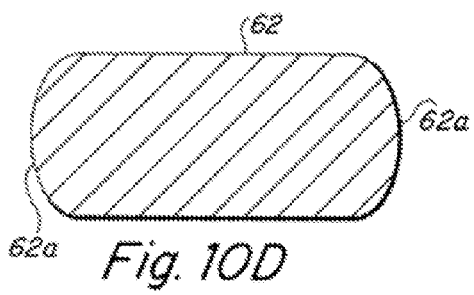
Fig. 10D
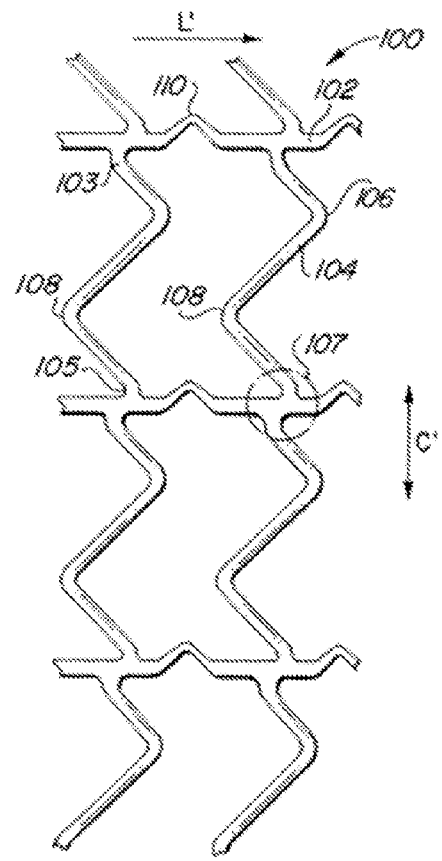
Fig. 11A
Fig. 11B

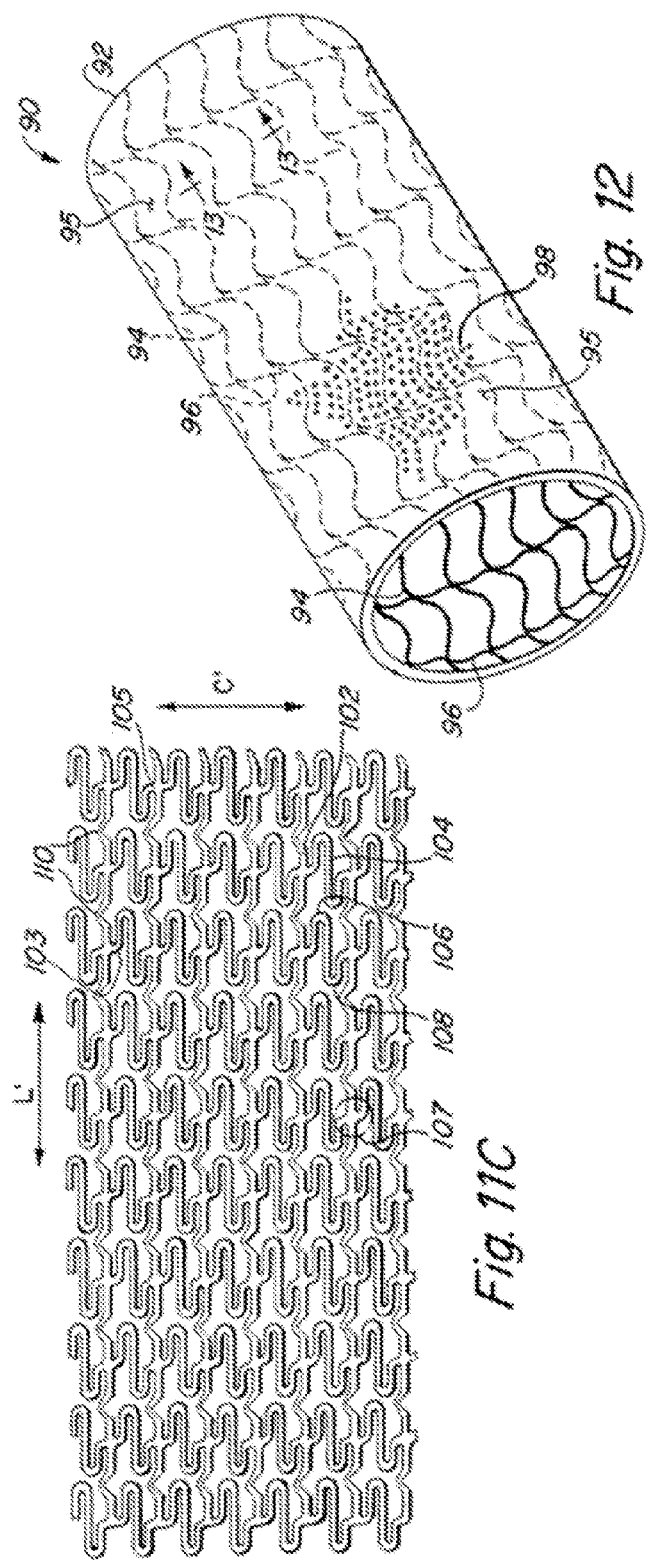
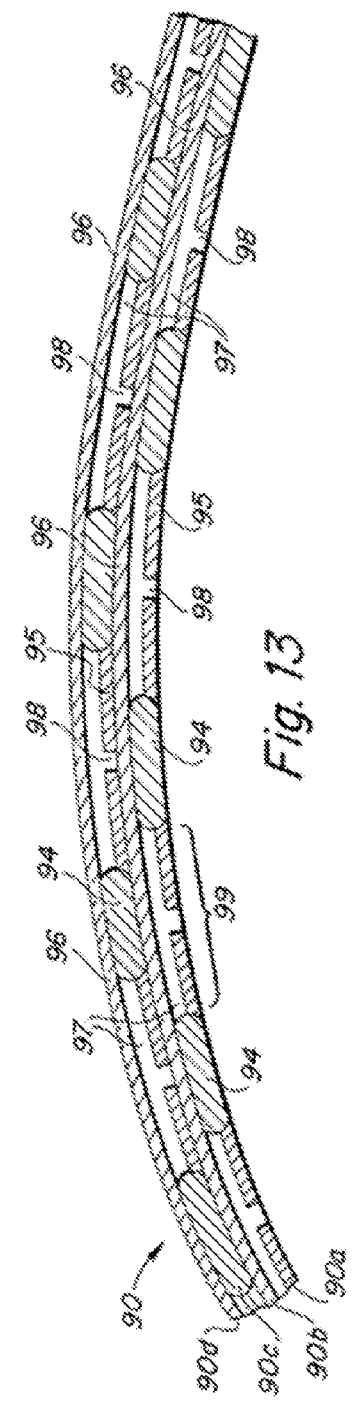
Fig. 11C
Fig. 12
Fig. 13

ENDOLUMINAL STENT, SELF-SUPPORTING ENDOLUMINAL GRAFT AND METHODS OF MAKING SAME

CROSS-REFERENCE TO RELATED APPLICATION

This application is a divisional application and corresponds to and claims priority of U.S. utility patent application Ser. No. 09/707,685, filed Nov. 7, 2000.

BACKGROUND OF THE INVENTION

The present invention relates generally to endoluminal stents and grafts designed for delivery into an anatomical passageway using minimally invasive techniques, such as percutaneous intravascular delivery using a delivery catheter passed over a guidewire. More particularly, the present invention relates to endoluminal stents having a scaffold structure and structural geometry which is particularly well-suited for providing physiologically acceptable radial or hoop strength and longitudinal flexibility, while also presenting a luminal surface thereof which presents less obstruction to longitudinal shear forces during fluid flow across the luminal surface of the inventive device while maximizing fatigue life and corrosion resistance.

Endoluminal stents are generally tubular scaffolds fabricated from implantable biocompatible materials. Stents have a generally tubular geometry characterized by a central lumen, a longitudinal axis, a circumferential axis and a radial axis. Conventional endoluminal stents fall within three general classifications: balloon expandable, self-expanding and shape-memory. Balloon expandable stents require mechanical intervention, such as by using a balloon catheter, to apply a positive pressure radially outward from a central lumen of the stent to mechanically deform the stent and urge it to a larger diameter. Self-expanding stents utilize inherent material mechanical properties of the stent material to expand the stent. Typically, self-expanding stents are fabricated of materials that rebound when a positive pressure is exerted against the material. Self-expanding stents are fabricated such that their zero-stress configuration conforms to the second larger diameter. The self-expanding stents are drawn down to the first smaller diameter and constrained within a delivery catheter for endoluminal delivery. Removal of the constraint releases the constraining pressure and the self-expanding stent, under its own mechanical properties, rebounds to the second larger diameter. Finally, shape-memory stents rely upon unique alloys that exhibit shape memory under certain thermal conditions. Conventional shape-memory stents are typically nickel-titanium alloys known generically as nitinol, which have a transition phase at or near normal body temperature, i.e., 37 degrees Centigrade.

The prior art is replete with various stent designs across all stent classifications. One of the difficulties with many conventional stent designs arises due to the conflicting criteria between the desired properties of circumferential or hoop strength of the stent, longitudinal or column strength, longitudinal flexibility, fish-scaling of individual structural members of the stent, fatigue life, corrosion resistance, corrosion fatigue, hemodynamics, radioopacity and biocompatibility and the capability of passing the stent through an already implanted stent. Typically, stents that are designed to optimize for hoop strength typically sacrifice either column strength and/or longitudinal flexibility, while stents that are designed to optimize for column strength often compromise longitudinal flexibility and/or hoop strength.

It has been found desirable to devise an endoluminal stent which employs a series of first and second structural elements arrayed in geometrical patterns which achieve a balance between hoop strength, column strength and longitudinal flexibility of the endoluminal stent. Many conventional stents employ a series of circumferential structural elements and longitudinal structural elements of varying configurations. A large number of conventional stents utilize circumferential structural elements configured into a serpentine configuration or a zig-zag configuration. The reason underlying this configuration is the need for radial expansion of the stent. Of these conventional stents which employ serpentine or zig-zag circumferential structural elements, many also employ longitudinal structural elements which join adjacent circumferential structural elements and provide a modicum of longitudinal or column strength while retaining longitudinal flexibility of the device. Additionally, many conventional stents require welds to join mating surfaces of the stent.

Heretofore, however, the art has not devised a unibody stent structural element geometry which achieves a balance between hoop strength, column strength and longitudinal flexibility, circumferential strength or hoop strength of the stent, longitudinal strength or column strength, longitudinal flexibility, fish-scaling of individual structural members of the stent, fatigue life, corrosion resistance, corrosion fatigue, hemodynamics, radioopacity, biocompatibility and the capability of passing the stent through an already implanted stent. The term "fish-scaling" is used in the art and herein to describe a condition where some stent structural elements extend beyond the circumferential plane of the stent during either radial expansion, implantation or while passing the stent through a bend in the vasculature. Those of ordinary skill in the art understand that fish-scaling of stent structural elements may cause the stent to impinge or snag upon the anatomical tissue either during endoluminal delivery or after implantation. The term "unibody" as used herein is intended to mean a stent that is fabricated without the use of welds and as an integral body of material.

The inventive endoluminal stent may be, but is not necessarily, fabricated by vapor deposition techniques. Vapor deposition fabrication of the inventive stents offers many advantages, including, without limitation, the ability to fabricate stents of complex geometries, the ability to control fatigue life, corrosion resistance, corrosion fatigue, bulk and surface material properties, and the ability to vary the transverse profiles, Z-axis thickness and X-Y-axis surface area of the stent's structural elements in manners that affect the longitudinal flexibility, hoop strength of the stent and radial expansion profiles.

SUMMARY OF THE INVENTION

Endoluminal stent and stent-graft design inherently attempts to optimize the functional aspects of radial expandability, i.e., the ratio of delivery diameter to expanded diameter, hoop strength, longitudinal flexibility, column strength, fish-scaling of individual structural members of the stent, fatigue life, corrosion resistance, corrosion fatigue, hemodynamics, biocompatibility and the capability of stent-through-stent delivery. Conventional stent designs have had to compromise one or more functional features of a stent in order to maximize a particular functionality, e.g., longitudinal flexibility is minimized in order to achieve desirable column strength or high hoop strengths are achieved at the expense of small ratios of radial expandability. It is an objective of the present invention to provide designs for endoluminal unibody stents that achieve balances between the ratio of radial expandability, hoop strength, longitudinal flexibility and column strength, with biocompatibility, hemodynamics, radioopacity, minimal or no fish-scaling and increased capacity for endothelialization.

The present invention consists generally of an endoluminal stent and self-supporting endoluminal graft each of which is formed from generally two interconnecting structural regions. First structural regions define circumferential sections of the endoluminal stent, provide the endoluminal stent with hoop strength, and are regions of relatively higher stent pattern density. The first structural regions are formed of a plurality of structural elements oriented circumferentially about the stent and are arrayed in adjacent, spaced-apart relationship with one another along the longitudinal axis of the endoluminal stent. Second structural regions define longitudinal support sections that interconnect adjacent circumferential sections in adjacent pairs of first structural regions and provide longitudinal or column strength to the endoluminal stent. The second structural regions are formed of a plurality of structural members oriented generally parallel to the longitudinal axis of the endoluminal stent and generally perpendicular to the orientation of the structural elements forming the first structural regions and are arrayed about the circumference of the endoluminal stent.

Two general embodiments of the stent of the present invention are disclosed. A first embodiment consists of second structural regions comprised of a plurality of longitudinal structural members each of which has a generally sinusoidal configuration along the longitudinal axis of the endoluminal stent, and the first structural regions are comprised of a plurality of sinusoidal structural elements that interconnect adjacent pairs of the structural elements of the second structural regions. This first embodiment is generally referred to herein as the "longitudinally flexible stent." A second embodiment consists of second structural regions comprised of a plurality of generally linear second structural members which extend the entire longitudinal axis of the endoluminal stent; the first structural regions are comprised of a plurality of sinusoidal structural elements which interconnect adjacent pairs of the plurality of generally linear second structural elements in spaced apart relationship. This second embodiment is generally referred to as the "columnar stent." For purposes of the present application, an individual structural element with a serpentine pattern or a zig-zag configuration having either regular or irregular periodicity or both in the some or all of the peaks and troughs is referred to as being "sinusoidal" or having a "sine-wave configuration."

In accordance with a first preferred embodiment of the inventive endoluminal stent, there is provided endoluminal stent that is comprised of a plurality of first structural elements that together form the circumference of the stent and extending along the longitudinal axis of the stent, and a plurality of second structural elements that interconnect adjacent pairs of first structural elements. Each of the plurality of first structural elements has a generally sinusoidal configuration with a regular or irregular periodicity or both between the peaks and troughs of the pattern, with the peaks and troughs projecting from the first structural elements in the circumferential axis. The plurality of second structural elements are generally linear members which interconnect an apex of a peak of one of the plurality of first structural elements with an apex of a valley of a second and adjacent one of the plurality of first structural elements. Each of the plurality of second structural elements are generally oriented parallel to the longitudinal axis of the stent.

The plurality of first structural elements is arrayed about and forms the circumference of the stent, with individual first structural elements extending parallel to the longitudinal axis of the stent. Each of the plurality of first structural elements preferably extends substantially the entire longitudinal axis of the stent, however, it is contemplated that some or all of the plurality of first structural elements may be oriented parallel to the longitudinal axis of the stent without extending substantially the entire longitudinal axis of the stent. Each of the plurality of first structural elements generally has a sine-wave configuration with the element being formed into successive peaks and troughs extending along the longitudinal axis of the stent. Again, it will be understood that the terms "sine-wave configuration" or "sinusoidal" are intended to include elements which have peaks and troughs with regular or irregular periodicity throughout the longitudinal axis of the element or which have peaks and troughs with regions of regular and regions of irregular periodicity along the longitudinal axis of the element, the peaks and troughs and the apices of the peaks and troughs may have many shapes, including, without limitation, regular curves, irregular curves, Z-shaped, U-shaped or the like. The plurality of first structural elements are arrayed in phase with one another, such that the peaks and troughs of one of the plurality of first structural elements in circumferentially aligned with the peaks and troughs of an adjacent first structural elements.

Each of the plurality of second structural elements comprises generally linear members which interconnect adjacent pairs of first structural elements. Each of the plurality of second structural elements is either integral with or conjoined with the first structural elements with which it is associated. Each of the plurality of second structural elements joins a trough of one first structural element with a peak of a second first structural element, with successive troughs of one first structural element being joined with successive peaks of the second first structural element.

Alternatively, in accordance with a second preferred embodiment of the present invention, the inventive endoluminal stent may consist of a plurality of substantially linear first structural elements oriented parallel to the longitudinal axis of the stent and a plurality of generally sinusoidal second structural elements which interconnect adjacent pairs of the first structural elements and extend generally about the circumferential axis of the stent. Each of the plurality of first structural elements preferably extends substantially the entire longitudinal axis of the stent, again, however, it is contemplated that some or all of the plurality of first structural elements may be oriented parallel to the longitudinal axis of the stent without extending substantially the entire longitudinal axis of the stent. The plurality of generally sinusoidal second structural elements form the circumferential links of the stent, and permit radial expansion, either by an applied radially outwardly directed force which plastically deforms the second structural elements, under inherent spring tension or as a result of shape memory properties of the stent material, or combinations thereof.

In accordance with all embodiments of the present invention, the plurality of first structural elements and the plurality of second structural elements may be fabricated of like biocompatible materials, preferably, biocompatible metals or metal alloys. In this manner, both the plurality of first structural elements and the plurality of second structural elements have like physical material properties, e.g., tensile strength, modulus of elasticity, plastic deformability, spring bias, shape memory or super-elastic properties. Alternatively, the plurality of first structural elements and the plurality of second structural elements may be fabricated of biocompatible materials, preferably, biocompatible metals or metal alloys which exhibit different physical or material properties. In this latter case, the plurality of first structural elements may, for example, be fabricated of a plastically deformable material, such as stainless steel, while the plurality of second structural elements are fabricated of a shape memory or super-elastic material, such as nickel-titanium alloys, or of a spring biased material, such as stainless steel.

Heretofore, joints between discrete sections of endoluminal stents required welds in order to join sections of the stent. One particular advantage of the present invention is that by forming the stent using vapor deposition techniques, not only are discrete sections atomically joined without the use of welds, but different materials may be employed in different and discrete sections of the stent in order to impart distinct material properties and, therefore, functionality, to the discrete sections.

Finally, the present invention also includes a self-supporting endoluminal graft. As used herein the term "graft" is intended to indicate any type of tubular member that exhibits integral columnar and circumferential strength and which has openings that pass through the thickness of the tubular member. The inventive self-supporting endoluminal graft preferably consists of a member formed of at least one of a plurality of layers, each layer being comprised of a plurality of first and second structural elements which intersect one another, as described above, to define a plurality of open regions between intersecting pairs of the first and second structural elements. A web region subtends at least a portion of the open region to at least partially enclose each of the plurality of open regions. Successive adjacent layers of the plurality of layers are positioned such that the open regions are staggered in the Z-axis transverse through the wall of the self-supporting endoluminal graft. By staggering the open regions, interlamellar spaces are created to facilitate endothelialization of the endoluminal graft.

BRIEF DESCRIPTION OF THE FIGURES

FIG. 10A is a diagrammatic cross-sectional view taken along line 10A-10A of FIG. 7 illustrating a first construction of the present invention.

FIG. 10B is a diagrammatic cross-sectional view taken along line 10B-10B of FIG. 7 illustrating a second construction of the present invention.

FIG. 10C is a diagrammatic cross-sectional view taken along line 10C-10C of FIG. 7 illustrating the Z-axis profile of each of the plurality of first structural elements of the present invention.

FIG. 10D is a diagrammatic cross-sectional view taken along line 10D-10D of FIG. 7 illustrating the Z-axis profile of each of the plurality of second structural elements of the present invention.

FIG. 11A is a fragmentary elevational view of an eighth embodiment of the present invention in its radially unexpanded state.

FIG. 11B is a fragmentary elevational view of the eighth embodiment of the present invention in its radially expanded state.

FIG. 11C is a side elevational view illustrating the eighth embodiment of the inventive endoluminal stent.

FIG. 12 is a perspective view of a self-supporting graft in accordance with the present invention.

FIG. 13 is a cross-sectional view taken along line 13-13 of FIG. 12.

DETAILED DESCRIPTION OF THE PREFERRED EMBODIMENTS

Figure 1:
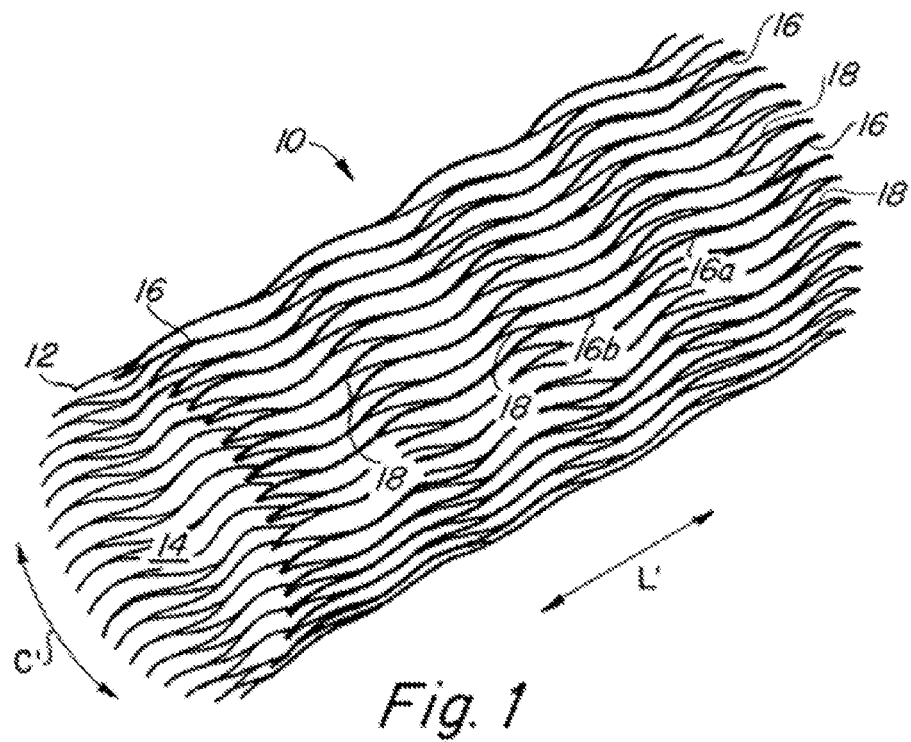
FIG. 1 is a perspective view of the inventive endoluminal stent.

In accordance with the present invention there is provided several preferred embodiments. In each of the preferred embodiments of the present invention, the general configuration of the inventive endoluminal stent is identical. With particular reference to FIG. 1, the inventive endoluminal stent 10 consists generally of a tubular cylindrical element having a stent wall 12 that defines a central lumen 14 of the stent. A plurality of first structural elements 16 are arrayed about the circumferential axis C' of the stent 10 and extend parallel along the longitudinal axis of stent 10. A plurality of second structural elements 18 interconnects adjacent pairs of the plurality of first structural elements 16. Each of the plurality of first structural elements 16 have a generally sinusoidal configuration with a plurality of peaks 16a and a plurality of troughs 16b of each first structural element. As noted above, the plurality of peaks 16a and the plurality of troughs 16b may have either regular or irregular periodicity along the longitudinal axis of each of the plurality of first structural elements 16 or each of the plurality of first structural elements 16 may have regions of regular periodicity and regions of irregular periodicity. Each of the plurality of second structural elements 18 preferably comprise linear elements which interconnect a peak 16a of a first one of the first structural elements 16 with a trough 16b of a second one of the first structural elements 16 adjacent the first one of the first structural elements 16.

The plurality of first 16 and second 18 structural elements are preferably made of materials selected from the group consisting of elemental titanium, vanadium, aluminum, nickel, tantalum, zirconium, chromium, silver, gold, silicon, magnesium, niobium, scandium, platinum, cobalt, palladium, manganese, molybdenum and alloys thereof, and nitinol and stainless steel. The plurality of first structural elements 16 and the plurality of second structural elements 18 may be made of the same material or of different materials and have the same material properties or have different material properties. The term "material properties" is intended to encompass physical properties, including without limitation, elasticity, tensile strength, mechanical properties, hardness, bulk and/or surface grain size, grain composition, and grain boundary size, intra and inter-granular precipitates. Similarly, the materials selected for the plurality of first structural elements 16 and the plurality of second structural elements 18 may be selected to have the same of different chemical properties. The term "chemical properties" is intended to encompass both any chemical reaction and change of state that the material may undergo after being implanted into a body and the physiological response of the body to the material after implantation.

The inventive stent 10, including the plurality of first structural elements 16 and second structural elements 18, is preferably made of a bulk material having controlled heterogeneities on the luminal surface thereof. As is described in co-pending, commonly assigned, U.S. patent application Ser. No. 09/443,929, filed Nov. 19, 1999, which is hereby incorporated by reference, heterogeneities are controlled by fabricating the bulk material of the stent to have defined grain sizes, chemical and intra and intergranular precipitates and where the bulk and surface morphology differ, yielding areas or sites along the surface of the stent while maintaining acceptable or optimal protein binding capability. The characteristically desirable properties of the inventive stent are: (a) optimum mechanical properties consistent with or exceeding regulatory approval criteria, (b) minimization of defects, such as cracking or pin hole defects, (c) a fatigue life of 400 MM cycles as measured by simulated accelerated testing, (d) corrosion and/or corrosion-fatigue resistance, (e) biocompatibility without having biologically significant impurities in the material, (f) a substantially non-frictional abluminal surface to facilitate atraumatic vascular crossing and tracking and compatible with transcatheter techniques for stent introduction, (g) radiopaque at selected sites and MRI compatible, (h) have a luminal surface which is optimized for surface energy and microtopography, (i) minimal manufacturing and material cost consistent with achieving the desired material properties, and (j) high process yields.

In accordance with the present invention, the foregoing properties are achieved by fabricating a stent by the same metal deposition methodologies as are used and standard in the microelectronics and nano-fabrication vacuum coating arts, and which are hereby incorporated by reference. The preferred deposition methodologies include ion-beam assisted evaporative deposition and sputtering techniques. In ion beam-assisted evaporative deposition it is preferable to employ dual and simultaneous thermal electron beam evaporation with simultaneous ion bombardment of the substrate using an inert gas, such as argon, xenon, nitrogen or neon. Bombardment with an inert gas, such as argon ions serves to reduce void content by increasing the atomic packing density in the deposited material during deposition. The reduced void content in the deposited material allows the mechanical properties of that deposited material to be similar to the bulk material properties. Deposition rates up to 20 nm/sec are achievable using ion beam-assisted evaporative deposition techniques.

When sputtering techniques are employed, a 200-micron thick stainless steel film may be deposited within about four hours of deposition time. With the sputtering technique, it is preferable to employ a cylindrical sputtering target, a single circumferential source that concentrically surrounds the substrate that is held in a coaxial position within the source. Alternate deposition processes which may be employed to form the stent in accordance with the present invention are cathodic arc, laser ablation, and direct ion beam deposition. When employing vacuum deposition methodologies, the crystalline structure of the deposited film affects the mechanical properties of the deposited film. These mechanical properties of the deposited film may be modified by post-process treatment, such as by, for example, annealing, high-pressure treatment or gas quenching.

Materials to make the inventive stents are chosen for their biocompatibility, mechanical properties, i.e., tensile strength, yield strength, and their ease of deposition include the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

During deposition, the chamber pressure, the deposition pressure and the partial pressure of the process gases are controlled to optimize deposition of the desired species onto the substrate. As is known in the microelectronic fabrication, nano-fabrication and vacuum coating arts, both the reactive and non-reactive gases are controlled and the inert or non-reactive gaseous species introduced into the deposition chamber are typically argon and nitrogen. The substrate may be either stationary or moveable, either rotated about its longitudinal axis, or moved in an X-Y plane within the reactor to facilitate deposition or patterning of the deposited material onto the substrate. The deposited material maybe deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve complex finished geometries of the resultant stent, both in the context of spatial orientation of the pattern as well as the material thickness at different regions of the deposited film, such as by varying the wall thickness of the material over its length to thicken sections at proximal and distal ends of the stent to prevent flaring of the stent ends upon radial expansion of the stent.

The stent may be removed from the substrate after stent formation by any of a variety of methods. For example, the substrate may be removed by chemical means, such as etching or dissolution, by ablation, by machining or by ultrasonic energy. Alternatively, a sacrificial layer of a material, such as carbon or aluminum, may be deposited intermediate the substrate and the stent and the sacrificial layer removed by melting, chemical means, ablation, machining or other suitable means to free the stent from the substrate.

The resulting stent may then be subjected to post-deposition processing to modify the crystalline structure, such as by annealing, or to modify the surface topography, such as by etching to affect and control the heterogeneities on the blood flow surface of the stent.

A plurality of microgrooves may be imparted onto the luminal and/or abluminal surface of the stent 10, as is more fully described in International Publication No. WO 99/23977, published 20 May 1999, which is commonly assigned with the present application and is hereby incorporated by reference. The plurality of microgrooves may be formed either as a post-deposition process step, such as by etching, or during deposition, such as by depositing the stent-forming material onto a mandrel which has a microtopography on the surface thereof which causes the metal to deposit with the microgroove pattern as part of the deposited material.

Each of the preferred embodiments of the present invention are preferably fabricated by employing a vapor deposition technique which entails vapor depositing a stent-forming metal onto a substrate. The substrate may be planar or cylindrical and is either pre-patterned with one of the preferred geometries of first and second structural elements, in either positive or negative image, or the substrate may be un-patterned. Where the substrate is un-patterned, the deposited stent-forming metal is subjected to post-deposition patterning to pattern the deposited stent-forming metal into one of the preferred geometries of the first and second structural elements. In all embodiments of the present invention fabricated by vapor deposition techniques, the need for post-deposition processing of the patterned endoluminal stent, e.g., modifying the surface of the stent by mechanical, electrical, thermal or chemical machining or polishing, is eliminated or minimized.

Vapor deposition fabrication of the inventive endoluminal stents offers many advantages, including, for example, the ability to fabricate stents of complex geometries, ultrafine dimensional tolerances on the order of Angstroms, the ability to control fatigue life, corrosion resistance, corrosion fatigue, inter- and intra-granular precipitates and their effect on corrosion resistance and corrosion fatigue, bulk material composition, bulk and surface material properties, radioopacity, and the ability to vary the transverse profiles, Z-axis thickness and X-Y-axis surface area of the stent structural elements in manners that affect the longitudinal flexibility, hoop strength, and radial expansion behavior and profile of the stent. Bulk material composition may be adjusted to employ elemental fractions in alloy compositions that are not feasible when using conventionally formed metals. This results in achieving the ability to tailor the alloy compositions in a manner that optimizes the alloy composition for a desired material or mechanical property. For example, nickel-titanium tubes exhibiting shape memory and/or superelastic properties were made employing in excess of 51.5 atomic percent nickel, which is not achievable using conventional working techniques due to high plateau stresses exhibited by the material. Specifically, the present inventors have fabricated nickel-titanium alloy tubes employing the method of the present invention that contain between 51.5 and 55 atomic percent nickel.

Vapor deposition of the inventive endoluminal stent, in accordance with a preferred embodiment of the present invention, significantly reduces or virtually eliminates inter- and intra-granular precipitates in the bulk material. It is common practice in the nickel-titanium endoluminal device industry to control transition temperatures and resulting mechanical properties by altering local granular nickel-titanium ratios by precipitation regimens. In the present invention, the need to control precipitates for mechanical properties is eliminated. Where nickel-titanium is employed as the stent-forming metal in the present invention, local nickel-titanium ratios will be the same or virtually identical to the nickel-titanium ratios in the bulk material, while still allowing for optimal morphology and eliminating the need for employing precipitation heat treatment. The resulting deposited stent-forming metal exhibits superior corrosion resistance, and hence, resistance to corrosion fatigue, when compared to conventional wrought nickel-titanium alloys.

The plurality of first structural elements 16 and the plurality of second structural elements 18 are preferably conformationally configured during vapor deposition to impart a generally ovular or elliptical transverse cross-sectional profile and have chamfered or curved leading and trailing luminal and abluminal surface edges in the longitudinal axis of the stent in order to provide better blood flow surface profiles.

Figure 2:
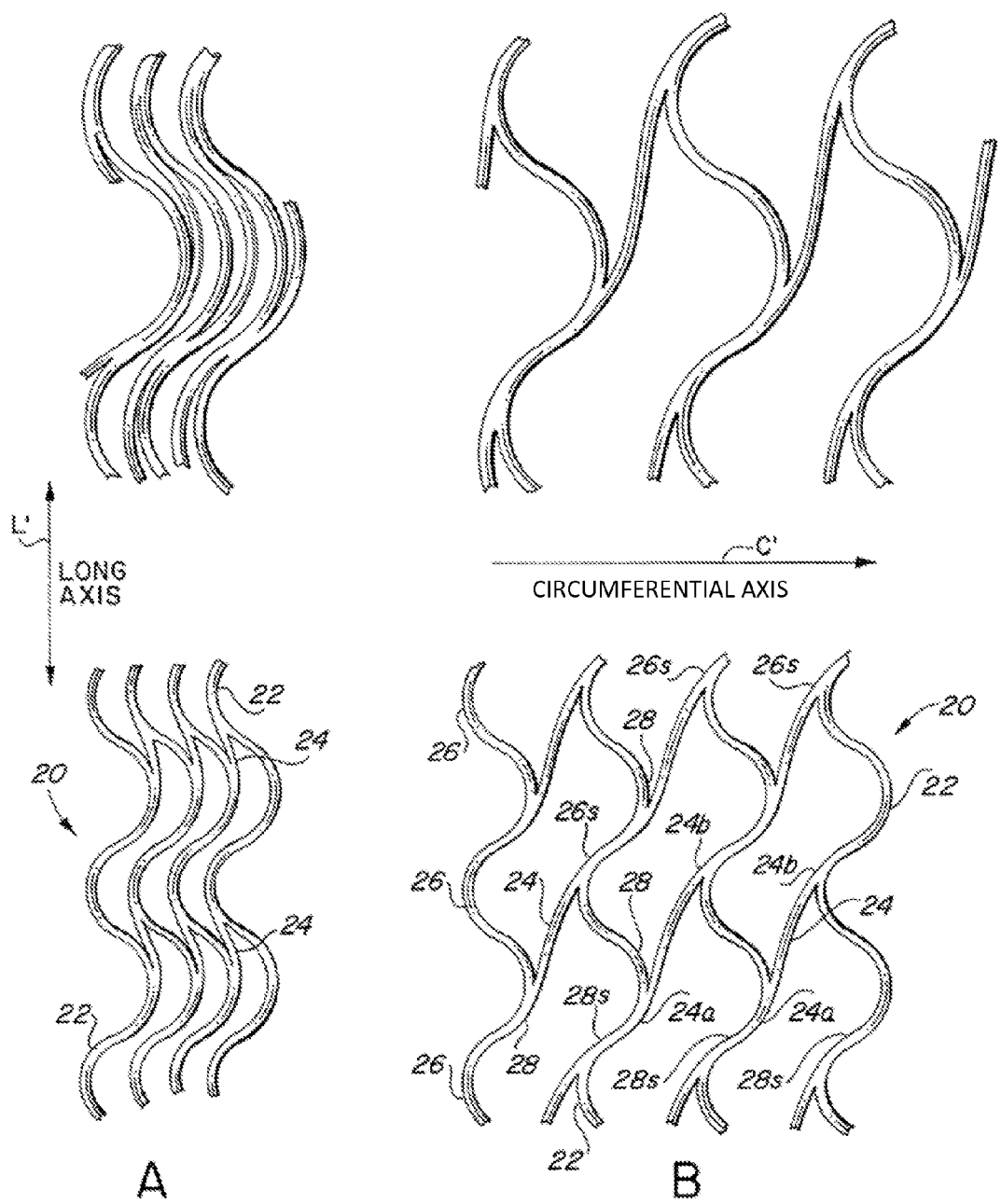
FIG. 2A is a fragmentary side elevational view of a first embodiment of the present invention depicting the inventive endoluminal stent in its radially unexpanded configuration.
FIG. 2B is a fragmentary side elevational view of the first embodiment of the present invention in its radially expanded configuration.
Figure 3:
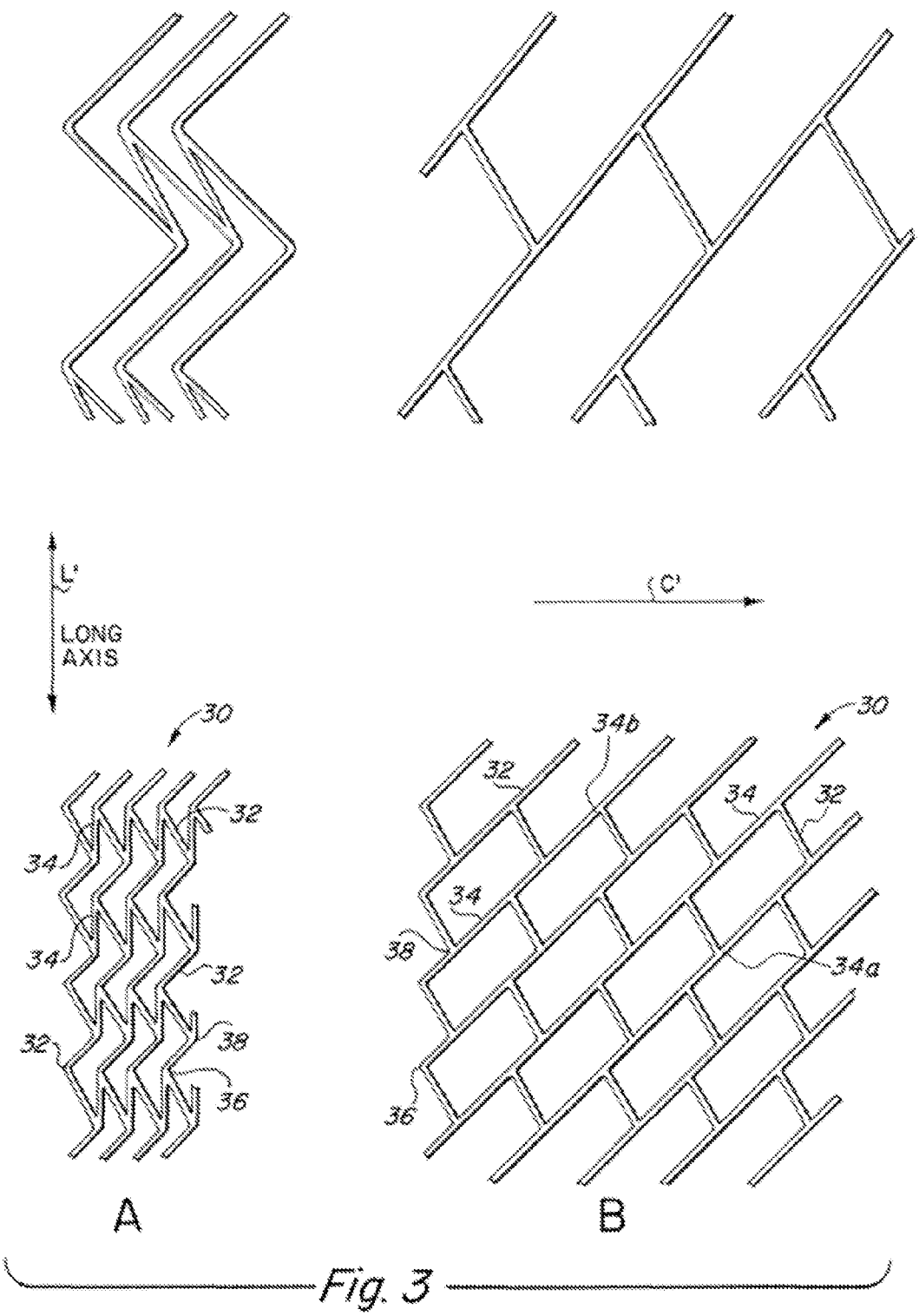
FIG. 3A is a fragmentary side elevational view of a second embodiment of the present invention in its radially unexpanded configuration.
FIG. 3B is a fragmentary side elevational view of the first embodiment of the present invention in its radially expanded configuration.
Figure 4:
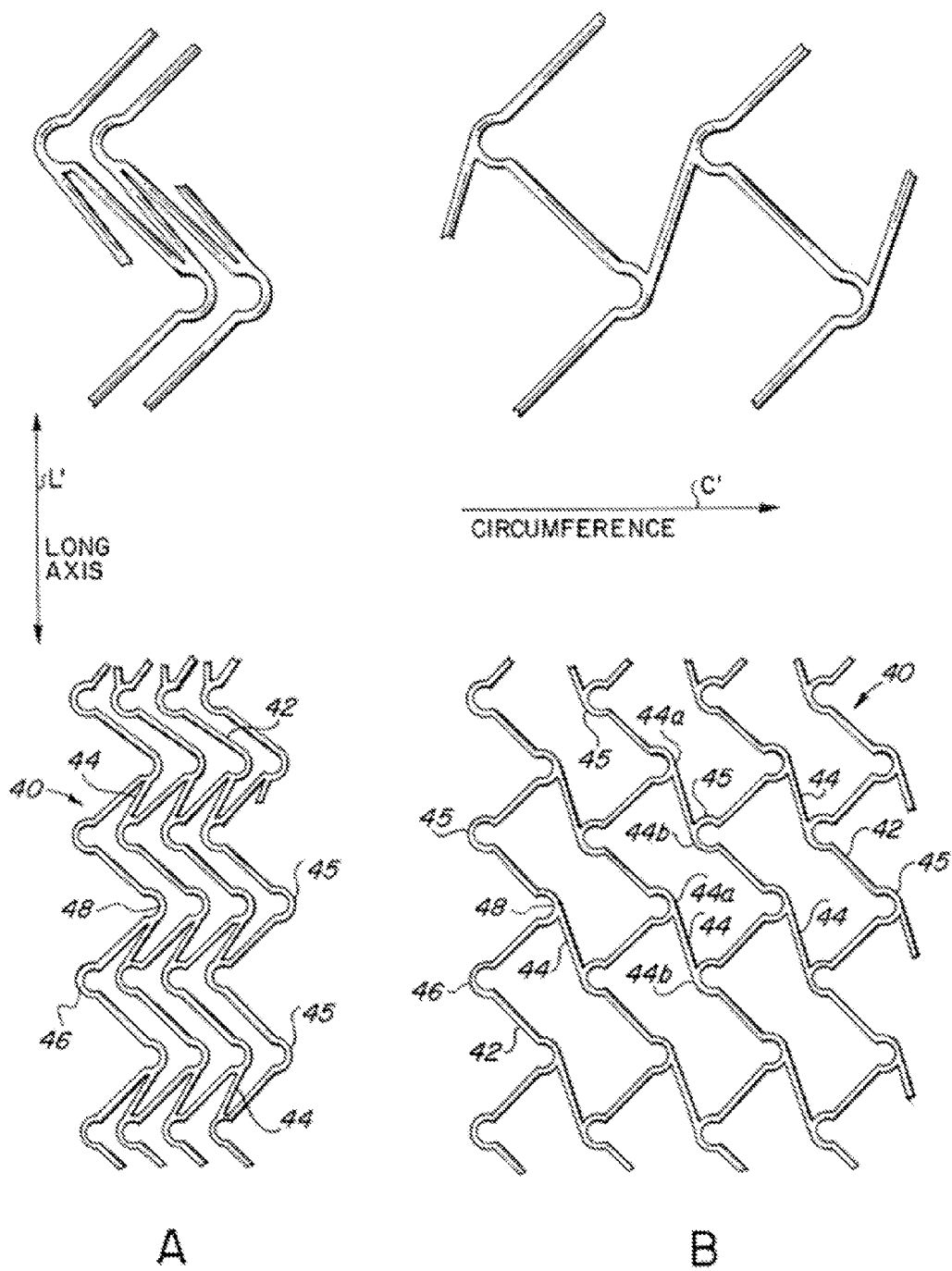
FIG. 4A is a fragmentary side elevational view of a third embodiment of the present invention in its radially unexpanded configuration.
FIG. 4B is a fragmentary side elevational view of the third embodiment of the present invention in its radially expanded configuration.

Turning to FIGS. 2-4, there are illustrated three preferred embodiments of the present invention. Each embodiment is depicted in its diametrically unexpanded state in the A Figure and in its diametrically expanded state in the B Figure. Thus, FIG. 2A represents a first embodiment of the inventive endoluminal stent in its diametrically unexpanded state, while FIG. 2B represents the first embodiment of the inventive endoluminal stent in its diametrically expanded state.

With specific reference to FIGS. 2A and 2B, there is illustrated stent 20 that consists of a plurality of first structural elements 22 and a plurality of second structural elements 24 which interconnect adjacent pairs of the plurality of first structural elements 22. Each of the plurality of first structural elements 22 extends parallel to the longitudinal axis L' of the stent 20, while each of the plurality of second structural elements 24 are arrayed in the circumferential axis C' of the stent 20. Each of the first structural elements 22 has a sinusoidal configuration consisting of a plurality of successive peaks 26 and troughs 28. The plurality of first structural elements 22 are arrayed about the circumference of stent 20 such that the peaks 26 and the troughs 28 of each individual first structural element 22 are in phase with respect to adjacent peaks 26 and troughs 28 of adjacent first structural elements 22.

The plurality of second structural elements 24 interconnect adjacent pairs of first structural elements 22. Each second structural element 24 has a first end 24a that connects with a trough 28 of a first structural element 22 and a second end 24b that connects with a peak 26 of an adjacent structural element 22. The plurality of second structural elements 24 serve to maintain the plurality of first structural elements in spaced-apart relationship relative to one another about the circumference of the stent 20. In accordance with a preferred embodiment of the invention, the first end 24a of a second structural element 24 couples to a trough 28 such that it is generally tangential to a downward slope 28s of the trough. Similarly, the second end 24b of the second structural element 24 couples to a peak 26 of a first structural element 22 such that the second structural element 24 is generally tangential to a downward slope 26s of the peak 26.

In the unexpanded state depicted in FIG. 2A, each of the plurality of second structural elements 24 have a generally S-shape or sinusoidal shape, however, when the stent is in its diametrically expanded state depicted in FIG. 2B, each of the plurality of second structural elements 24 assumes a generally linear configuration which serves to maintain an enlarged spacing between adjacent pairs of first structural elements 22 relative to when the stent 20 is in its unexpanded state.

Turning to FIGS. 3A and 3B, there is illustrated a second preferred embodiment of the stent 30 present invention. Like stent 20 described above, stent 30 consists generally of a plurality of first structural elements 32 and a plurality of second structural elements 34 which interconnect adjacent pairs of the plurality of first structural elements 32. Each of the plurality of first structural elements 32 extends parallel to the longitudinal axis L' of the stent 30, while each of the plurality of second structural elements 34 are arrayed in the circumferential axis C' of the stent 30. Each of the first structural elements 32 has a generally sinusoidal zigzag or Z-configuration consisting of a plurality of successive peaks 36 and troughs 38. The plurality of first structural elements 32 are arrayed about the circumference of stent 30 such that the peaks 36 and the troughs 38 of each individual first structural element 32 are in phase with respect to adjacent peaks 36 and troughs 38 of adjacent first structural elements 32.

The plurality of second structural elements 34 interconnect adjacent pairs of first structural elements 32. Each second structural element 34 has a first end 34*a*, which connects with a trough 38 of a first structural element 32, and a second end 34*b*, which connects with a peak 36 of an adjacent structural element 32. The plurality of second structural elements 34 serve to maintain the plurality of first structural elements 32 in spaced-apart relationship relative to one another about the circumference of the stent 30.

In the unexpanded state depicted in FIG. 3A, each of the plurality of second structural elements 34 have a generally linear configuration which is positioned substantially parallel to the longitudinal axis L' of the stent 30. However, when the stent 30 is in its diametrically expanded state depicted in FIG. 3B, each of the plurality of second structural elements 34 repositions to assume a generally circumferential orientation relative to the stent which, in turn, serves to maintain an enlarged spacing between adjacent pairs of first structural elements 32 relative to when the stent 30 is in its unexpanded state.

Turning to FIGS. 4A and 4B, there is illustrated a third preferred embodiment of the stent 40 present invention. Like stents 20 and 30 described above, stent 40 consists generally of a plurality of first structural elements 42 and a plurality of second structural elements 44 which interconnect adjacent pairs of the plurality of first structural elements 42. Each of the plurality of first structural elements 42 extends parallel to the longitudinal axis L' of the stent 40, while each of the plurality of second structural elements 44 are arrayed in the circumferential axis C' of the stent 40. Each of the first structural elements 42 has a generally sinusoidal zig-zag or Z-configuration consisting of a plurality of successive peaks 46 and troughs 48. Arcuate sections 45 are provided at apices of each of the peaks 46 and the troughs 48. The arcuate sections 45 act as springs for each first structural element 42 to impart axial flexibility and longitudinal compressibility and expandability to the stent 40. The plurality of first structural elements 42 are arrayed about the circumference of stent 40 such that the peaks 46 and the troughs 48 of each individual first structural element 42 are in phase with respect to adjacent peaks 46 and troughs 48 of adjacent first structural elements 42.

The plurality of second structural elements 44 interconnect adjacent pairs of first structural elements 42. Each second structural element 44 has a first end 44*a*, which connects with an arcuate section 45 of a trough 48 of a first structural element 42, and a second end 44*b*, which connects with an arcuate section 45 of a peak 46 of an adjacent first structural element 42. The plurality of second structural elements 44 serve to maintain the plurality of first structural elements 42 in spaced-apart relationship relative to one another about the circumference of the stent 40.

In the unexpanded state depicted in FIG. 4A, each of the plurality of second structural elements 44 have a generally linear configuration and are oriented substantially parallel to adjacent sections of the first structural elements 42 to which it is attached. However, when the stent 40 is in its diametrically expanded state depicted in FIG. 4B, each of the plurality of second structural elements 44 repositions to assume an orientation which is generally parallel to the longitudinal axis L' of the stent 40 and serves to maintain an enlarged spacing between adjacent pairs of first structural elements 42 reltive to when the stent 40 is in its unexpanded state.

Figure 5:
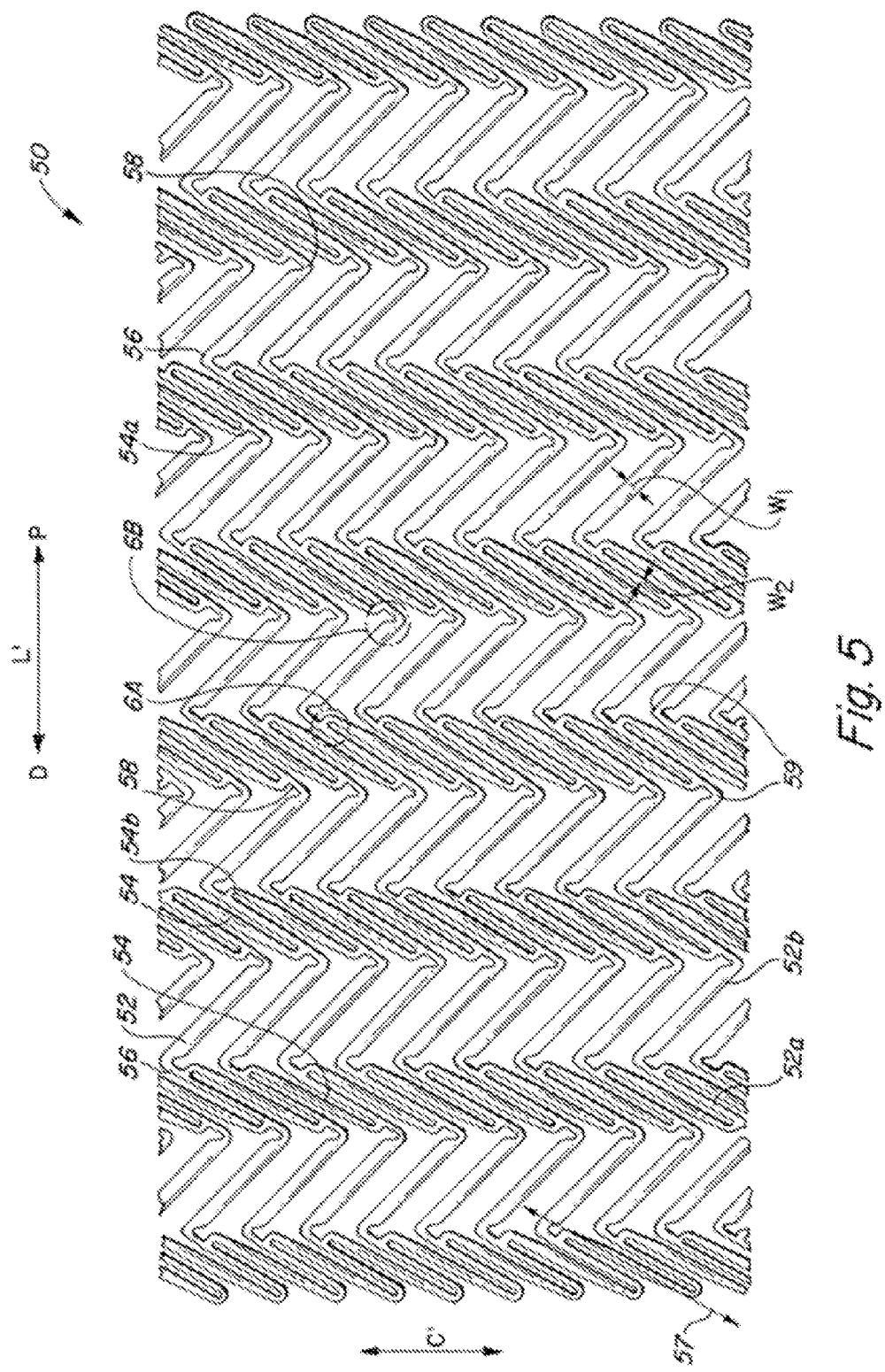
FIG. 5 is a side elevational view of a portion of a fourth embodiment of the present invention in its radially unexpanded configuration.
Figure 6A:
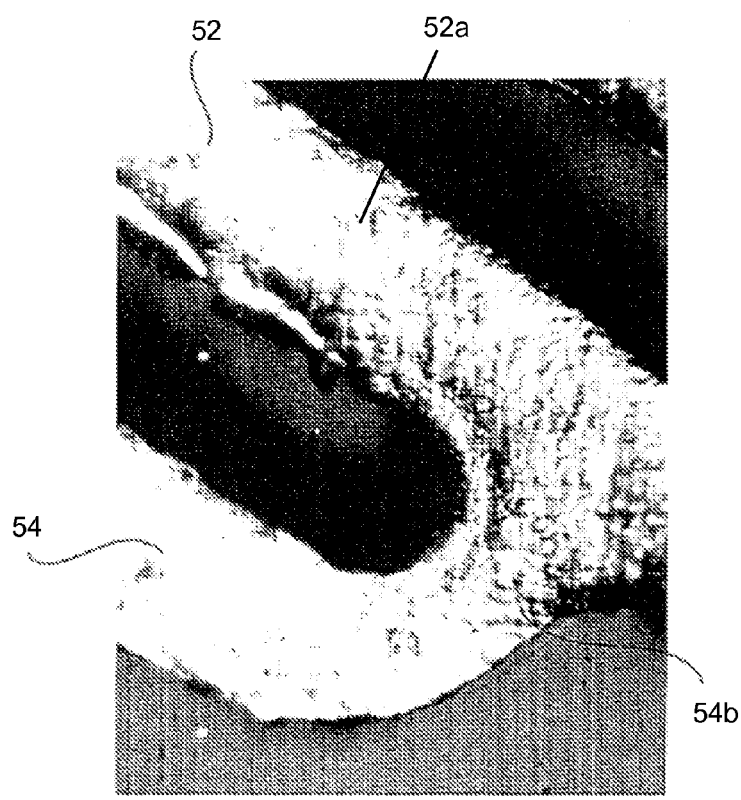
FIG. 6A is a photomicrograph of section 6A in FIG. 5.
Figure 6B:
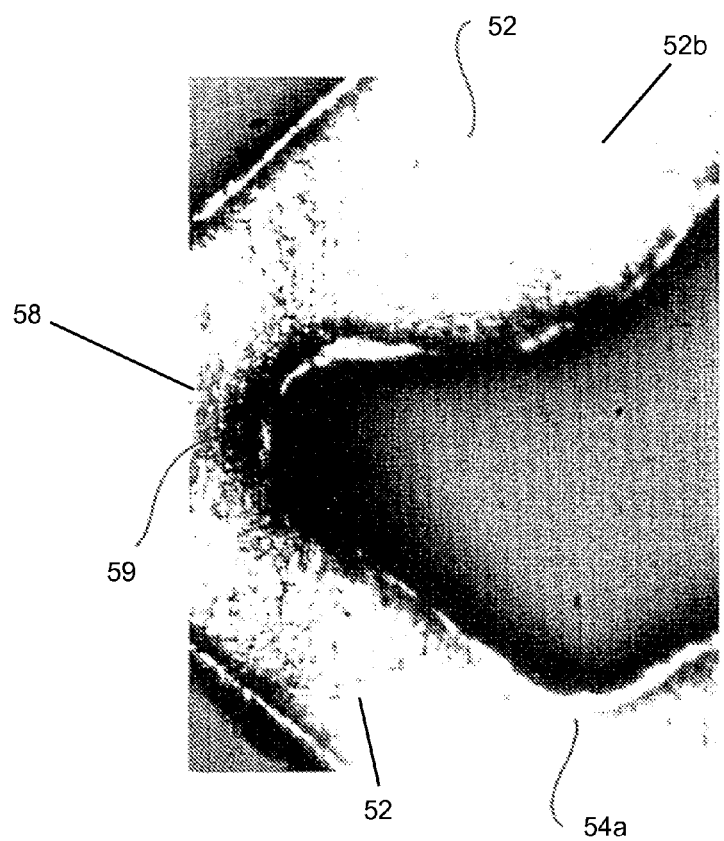
FIG. 6B is a photomicrograph of section 6B in FIG. 5.

FIGS. 5, 6A and 6B depict another preferred embodiment and the best mode contemplated for the present invention. Like stents 20, 30 and 40 described above, stent 50 consists generally of a plurality of first structural elements 52 and a plurality of second structural elements 54 which interconnect adjacent pairs of the plurality of first structural elements 52. Each of the plurality of first structural elements 52 extends parallel to the longitudinal axis L' of the stent 50, while each of the plurality of second structural elements 54 are arrayed in the circumferential axis C' of the stent 50. Each of the first structural elements 52 has a generally sinusoidal zig-zag or Z-configuration consisting of a plurality of successive peaks 56 and troughs 58. The plurality of first structural elements 52 are arrayed about the circumference of stent 50 such that the peaks 56 and the troughs 58 of each individual first structural element 52 are in phase with respect to adjacent peaks 56 and troughs 58 of adjacent first structural elements 52.

The plurality of second structural elements 54 interconnect adjacent pairs of first structural elements 52. Each second structural element 54 has a first end 54*a*, which connects with a trough 58 of a first structural element 52, and a second end 54*b* that connects with a peak 56 of an adjacent first structural element 52. The plurality of second structural elements 54 serve to maintain the plurality of first structural elements 52 in spaced-apart relationship relative to one another about the circumference of the stent 50.

In the unexpanded state depicted in FIG. 5, each of the plurality of second structural elements 54 have a generally linear configuration which is positioned substantially parallel to the longitudinal axis L' of the stent 50. For purposes of explanation and illustration only, the stent 50 is also referenced with proximal P and distal D orientations relative to the longitudinal axis L' of the stent 50.

When the stent 50 is in its diametrically expanded state, each of the plurality of second structural elements 54 repositions to assume a generally circumferential orientation relative to the stent which, in turn, serves to maintain an enlarged spacing between adjacent pairs of first structural elements 52 relative to when the stent 50 is in its unexpanded state.

Each of the plurality of first structural elements 52 further comprise alternating relatively narrower sections 52*a* and relatively wider sections 52*b* which form each peak 56 and each trough 58 of each first structural element 52. In accordance with the best mode presently contemplated for the present invention, and without limiting the scope of the invention, the preferred ratio of surface area between the wider sections 52*b* and the narrower sections 52*a* is about 2:1. Thus, for example, if the width $W_2$ of the narrower section 52*a* is about 60i, the width $W_1$ of the wider section 52*b* will be about 120i. The apices of each peak 56 and each trough 58 are formed by a chamfer or taper 59 between the narrower section 52*a* and the wider section 52*b* of each peak 56 and each trough 58 of each of the plurality of first structural elements 52. The apex of a typical peak 56 and trough 58 and the chamfered or tapered section 59, described above, is depicted in the scanning electron photomicrograph at FIG. 6B.

Each of the plurality of second structural elements 54 has a generally elongate configuration that connects at a first end 54*a* to a trough 58 and at a second end 54*b* to a peak 56. Each of the first end 54*a* and the second end 54*b* connect to adjacent first structural elements 52 and are formed by chamfered sections which project generally at right angles relative to a central longitudinal axis 57 of each of the plurality of second structural elements 54 and connect to a terminal section of the narrower section 52*a* of either each peak 56 or each trough 58 of each of the plurality of the first structural elements 52. FIG. 6A depicts with greater particularity a second end 54*b* and the chamfered section integrally connecting a second structural element 54 with a first structural element 52. The chamfered sections at first end 54*a* and second end 54*b* project in opposing directions relative to one another. Thus, in one embodiment the chamfered section at the first end 54*a* projects generally distally relative to the longitudinal axis L' of stent 50, while the chamfered section at the second end 54*b* projects generally proximally relative to the longitudinal axis L' of stent 50. Those of ordinary skill in the art will understand that the relative directional orientation of the first end 54*a* and the second end 54*b* may be switched so that the first end 54*a* projects generally proximally while the second end 54*b* projects generally distally relative to the longitudinal axis L' of stent 50. Similarly, those of ordinary skill in the art will appreciate that alternate configurations for the first end 54*a* and the second end 54*b* are contemplated by the present invention. For example, instead of a generally perpendicular orientation between the chamfered section and the longitudinal axis 57 of the second structural element 54, the first end 54*a* and the second end 54*b* could have alternate angular orientations relative to the first structural element 52 and the second structural element 54.

Turning to FIGS. 7-10, there are illustrated alternate preferred embodiments of the present invention in which a plurality of first structural elements are generally linear members which extend parallel to a longitudinal axis L' of the stent and a plurality of second structural elements which have a generally sinusoidal shape form the circumferential axis C' of the stent and permit radial expansion thereof. These alternate preferred embodiments exhibit excellent column strength due to the linear members of the plurality of first structural elements while the configuration of the plurality of second structural elements facilitate low device delivery profiles while allowing for large ratios of radial expansion over the stent's unexpanded diameter.

Figure 7:
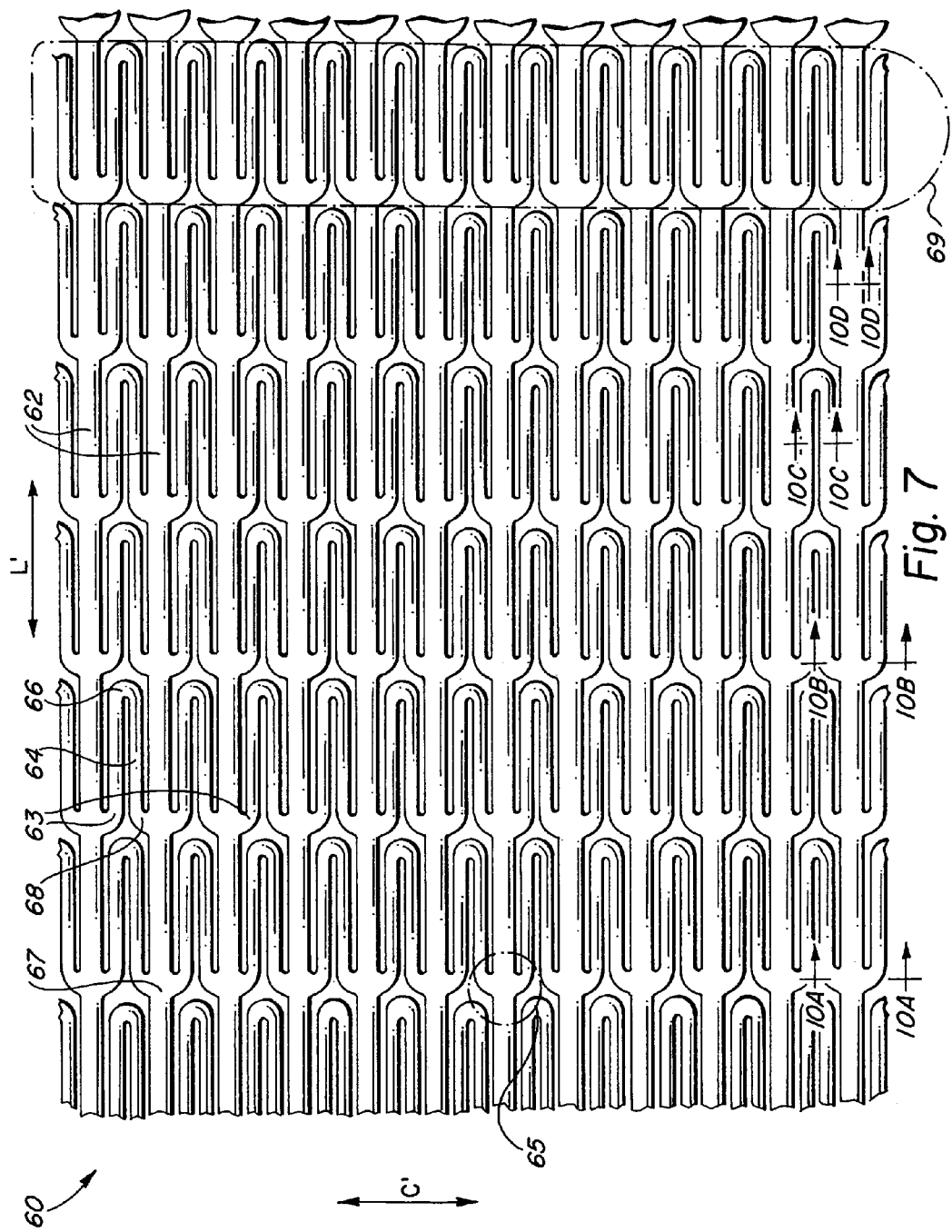
FIG. 7 is a fragmentary side elevational view of a fifth embodiment of the present invention in its radially unexpanded configuration.

With particular reference to FIG. 7, there is illustrated a stent 60 which includes a plurality of generally linear first structural elements 62 which extend parallel to and substantially the entire the longitudinal axis L' of the stent 60. The circumferential axis C' of the stent 60 is comprised of a plurality of second structural elements 64, each of which has a generally U-shaped configuration. Individual second structural elements 64 interconnect adjacent pairs of first structural elements 62 and maintain the first structural elements 62 in spaced apart relationship from one another. Each individual second structural element 64 is composed of an apex 66, which forms the peak of each second structural element 64, a first connection section 63 and a second connection section 68. The first connection section 63 connects the second structural element 64 to a single first structural element 62, while the second connection section 68 connects the second structural element 64 to an adjacent first structural element 62, thereby maintaining the first structural elements 62 in spaced apart relationship relative to one another. Each of the plurality of second structural elements 64 are either integral with or connected to each of the plurality of first structural elements 62 at intersection points 67 along the circumferential axis C' of the stent 60. A plurality of second structural elements 64 are aligned in end-to-end fashion, with the first connection section 63 of one second structural element 64 being adjacent to a second connection section 68 of another second structural element 64, thereby forming a continuous sinusoidal circumferential element 69 which extends about the entire circumferential axis C' of the stent 60. In the continuous sinusoidal circumferential element 69, peaks of each sinusoidal period are formed by the apices 66 of each generally U-shaped second structural element 64, while troughs 65 of each sinusoidal period are formed by the first connection section 63 of one second structural element 64, the second connection section 68 of another second structural element 64, and their connection point 67 on the first structural element 62.

A plurality of continuous sinusoidal circumferential elements 69 are arrayed in spaced apart relationship along the longitudinal axis L' of the stent 60 and form the walls of the stent 60. During radial expansion of the stent 60, each of the plurality of second structural elements 64 extends circumferentially along circumferential axis C' such that the periodicity between successive peaks of each generally U-shaped second structural element 64 increases.

In accordance with this preferred embodiment of stent 60, the apices 66 of each second structural member 64, which form the peak of each sinusoidal period, have a common directional orientation parallel to and directed either proximally or distally relative to the longitudinal axis L' of the stent 60. In accordance with a variation of the preferred embodiment of the stent 60, the apices 66 of each second structural member 64 in a first continuous sinusoidal circumferential element 69 are directionally oriented opposite that of the apices 66 of each second structural member 64 in a second, adjacent, continuous sinusoidal circumferential element 69. In this variation, adjacent continuous sinusoidal circumferential elements 69 would be out-of-phase relative to one another, i.e., such as with a sine and cosine functions, with the apices 66 of each sinusoidal element being adjacent one another and one apex 66 oriented proximally and a longitudinally adjacent apex 66 being oriented distally relative to the longitudinal axis L' of the stent 60.

Figure 8:
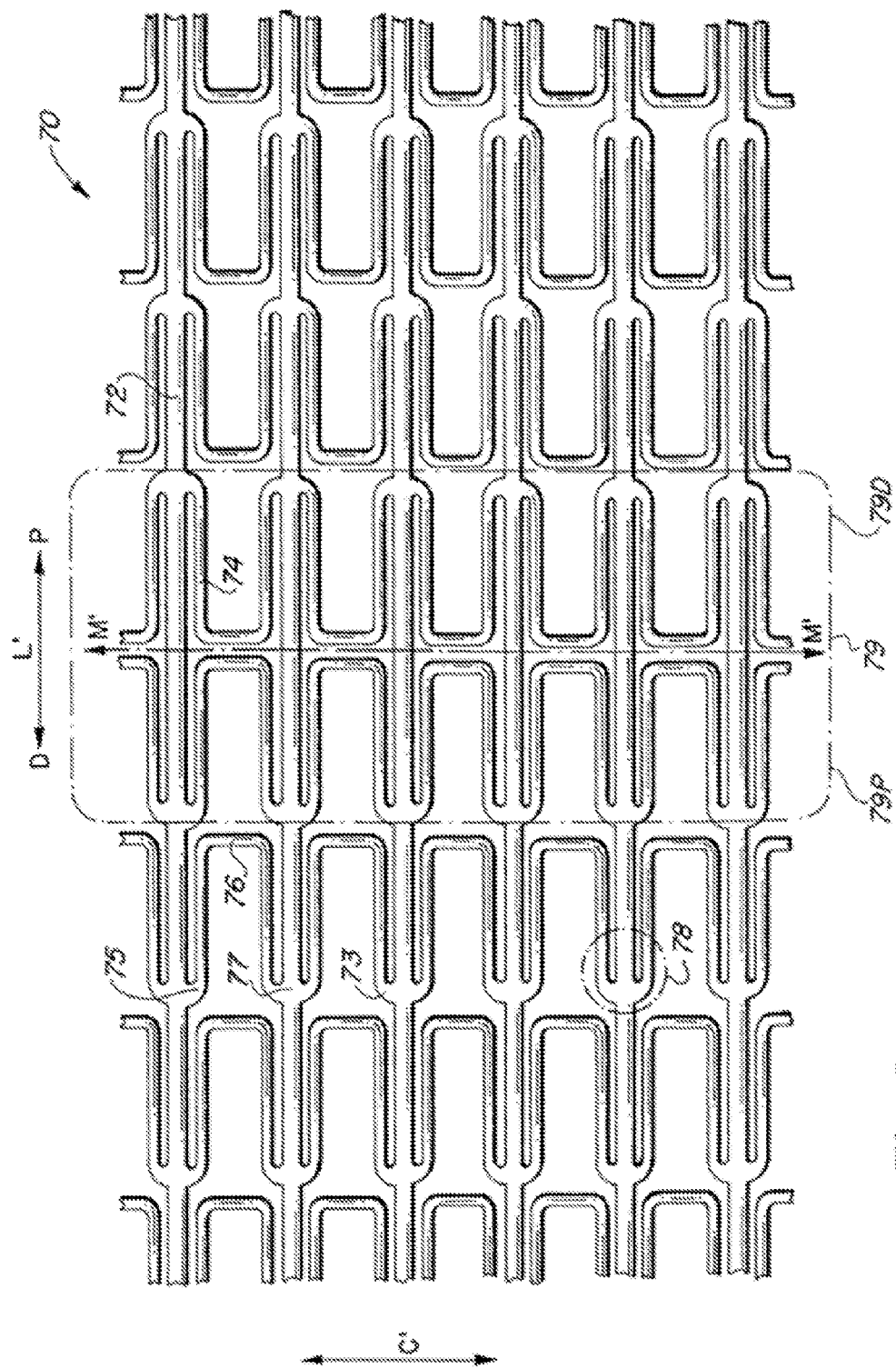
FIG. 8 is a fragmentary side elevational view of a sixth embodiment of the present invention in its radially unexpanded configuration.

With particular reference to FIG. 8, there is illustrated an alternate embodiment of the present invention in which a stent 70 is comprised of a plurality of plurality of generally linear first structural elements 72 which extend parallel to and substantially the entire longitudinal axis L' of the stent 70. The circumferential axis C' of the stent 70 is comprised of a plurality of second structural elements 74, each of which has a generally U-shaped configuration. Individual second structural elements 74 interconnect adjacent pairs of first structural elements 72 and maintain the first structural elements 72 in spaced apart relationship from one another. Each individual second structural element 74 is composed of an apex 76, which forms the peak of each second structural element 74, a first connection section 73 and a second connection section 75. As distinguished from stent 60, in which the apices 66 have a regular curve, each of the apices 76 of stent 70 are formed by generally linear sections which are oriented parallel to the circumferential axis C' of stent 70.

The first connection section 73 connects the second structural element 74 to a single first structural element 72, while the second connection section 75 connects the second structural element 74 to an adjacent first structural element 72, thereby maintaining the first structural elements 72 in spaced apart relationship relative to one another. Each of the plurality of second structural elements 74 are either integral with or connected to each of the plurality of first structural elements 72 at intersection points 77 along the circumferential axis C' of the stent 70.

A plurality of second structural elements 74 are aligned in end-to-end fashion, with the first connection section 73 of one second structural element 74 being adjacent to a second connection section 75 of another second structural element 74, thereby forming a continuous sinusoidal circumferential element 79 which extends about the entire circumferential axis C' of the stent 70. In the continuous sinusoidal circumferential element 79, peaks of each sinusoidal period are formed by the apices 76 of each generally U-shaped second structural element 74, while troughs 78 of each sinusoidal period are formed by the first connection section 73 of one second structural element 74, the second connection section 75 of another second structural element 74, and their connection point 77 on the first structural element 72.

A plurality of continuous sinusoidal circumferential elements 79 are arrayed in spaced apart relationship along the longitudinal axis L' of the stent 70 and form the walls of the stent 70. During radial expansion of the stent 70, each of the plurality of second structural elements 74 extends circumferentially along circumferential axis C' such that the periodicity between successive peaks of each generally U-shaped second structural element 74 increases.

In accordance with this preferred embodiment of stent 70, the continuous sinusoidal circumferential elements 79 are categorized into a plurality of proximal sinusoidal circumferential elements $79_p$ and a plurality of distal sinusoidal circumferential elements $79_d$. The sole difference between the proximal $79_p$ and the distal $79_d$ sinusoidal circumferential elements is the directional orientation of the apices 76 of each second structural member 74 relative to the longitudinal axis L' of the stent 70. That is, in the plurality of proximal circumferential elements $79_p$, the apex 76 is oriented toward the proximal end of the stent 70, while in the plurality of distal circumferential elements $79_d$, the apex 76 is oriented toward the distal end of the stent 70. Either at a medial line M' of the stent 70 or at spaced apart longitudinal sections of the stent 70, a proximal sinusoidal circumferential element $79_p$ is longitudinally adjacent a distal sinusoidal circumferential element $79_d$ such that apices 76 of each of the proximal sinusoidal circumferential element $79_p$ are proximate the apices 76 of the adjacent distal sinusoidal circumferential element $79_d$, i.e., as in a sine and cosine function. In this configuration, stent 70 will have added longitudinal flexibility either at the medial line M' or at the spaced apart longitudinal sections of the stent 70 where the plurality of proximal sinusoidal circumferential elements $79_p$ and the plurality of distal sinusoidal circumferential elements $79_d$ are out of phase relative to one another.

Figure 9:
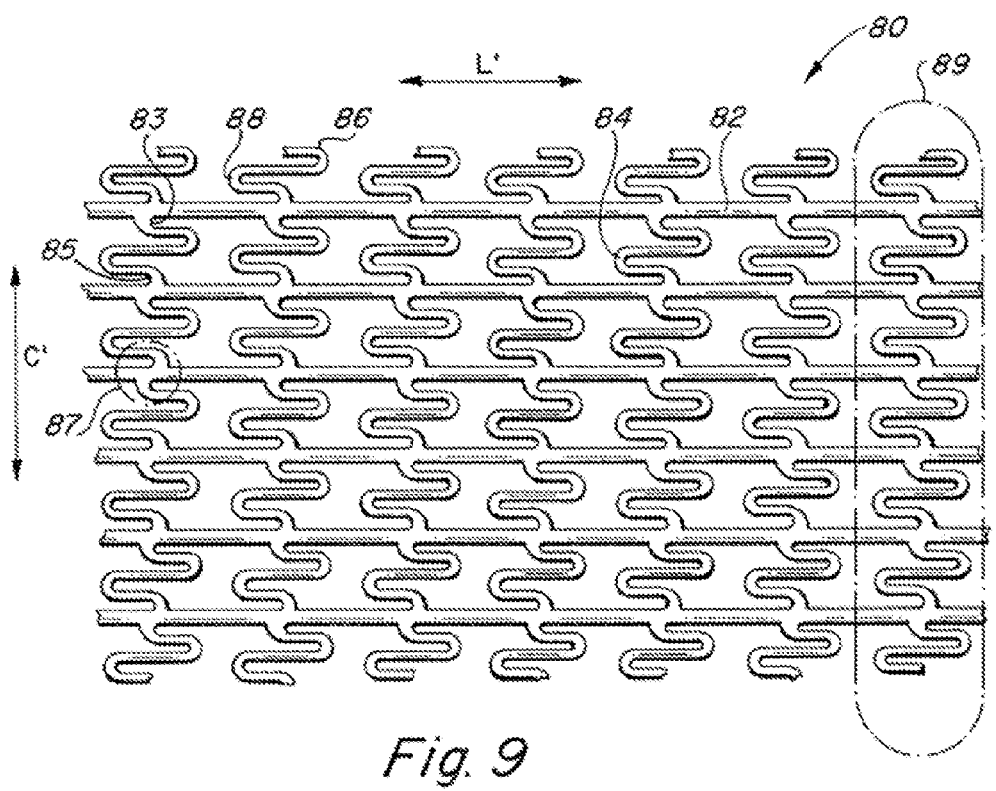
FIG. 9 is a fragmentary side elevational view of a seventh embodiment of the present invention in its radially unexpanded configuration.

Turning now to FIG. 9, there is illustrated a stent 80 which includes a plurality of generally linear first structural elements 82 which extend parallel to and substantially the entire longitudinal axis L' of the stent 80. The circumferential axis C' of the stent 80 is comprised of a plurality of second structural elements 84, each of which has a generally S-shaped or sine-wave configuration. Individual second structural elements 84 interconnect adjacent pairs of first structural elements 82 and maintain the first structural elements 82 in spaced apart relationship from one another. Each individual second structural element 84 is composed of at least two apices 86, 88, which project in opposing directions relative to the longitudinal axis L' of the stent 80, a first connection section 83 and a second connection section 85. The first connection section 83 connects the second structural element 84 to a single first structural element 82, while the second connection section 85 connects the second structural element 84 to an adjacent first structural element 82, thereby maintaining the first structural elements 82 in spaced apart relationship relative to one another. Each of the plurality of second structural elements 84 are either integral with or connected to each of the plurality of first structural elements 82 at intersection points 87 along the circumferential axis C' of the stent 80. A plurality of second structural elements 84 are aligned in end-to-end fashion, with the first connection section 83 of one second structural element 84 being adjacent to a second connection section 85 of another second structural element 84, thereby forming a continuous circumferential element 89 which extends about the entire circumferential axis C' of the stent 80. A plurality of continuous circumferential elements 89 are arrayed in spaced apart relationship along the longitudinal axis L' of the stent 80 and form the walls of the stent 80.

In accordance with this preferred embodiment of stent 80, the apices 86 of each second structural element 84 have a common directional orientation parallel to and directed either proximally or distally relative to the longitudinal axis L' of the stent 80. Similarly, the apices 88 of each second structural element 84 have a common directional orientation parallel to and directed either proximally or distally relative to the longitudinal axis L' of the stent 80. Thus, all apices 86 and all apices 88 are in phase relative to like apices on longitudinally adjacent second structural elements 84. In accordance with a variation of the preferred embodiment of the stent 80, the apices 86 of each second structural element 84 in a first continuous circumferential element 89 are directionally oriented opposite that of the apices 86 of each second structural element 84 in a second, adjacent, continuous circumferential element 89. In this variation, adjacent continuous circumferential elements 89 would be out-of-phase relative to one another, i.e., such as with a sine and cosine functions, with the apices 86 of each second structural element 84 being longitudinally adjacent one another and one apex 86 oriented proximally and a longitudinally adjacent apex 86 being oriented distally relative to the longitudinal axis L' of the stent 80.

FIGS. 10A and 10B illustrate alternate constructions of the inventive stent. For purposes of the following discussion, it will be noted that the particular stent geometry is a matter of choice and includes, but is not limited to the inventive stents 10, 20, 30, 40, 50, 60, 70 and 80 described above. As noted above, the stent of the present invention may be fabricated of materials selected from the group consisting of elemental titanium, vanadium, aluminum, nickel, tantalum, zirconium, chromium, silver, gold, silicon, magnesium, niobium, scandium, platinum, cobalt, palladium, manganese, molybdenum, and alloys thereof, nitinol and stainless steel. Because the method of making the inventive stent involves utilizing vacuum deposition technologies well known in the microelectronics arts, either a single material may be employed or plural materials may be employed to make either or both the plurality of first structural elements 62 and the plurality of second structural elements 64 or portions thereof. Where plural materials are employed in the vacuum deposition fabrication of a stent, such as, for example, inventive stents 10, 20, 30, 40, 50, 60, 70 or 80, intersection points 67, for example, between first structural elements 62 and the first connection end 63 of one second structural element 64 and a second connection end 68 of another second structural element 64 may be either as a monolayer of alloyed metals used to form the first structural element 62 and the second structural element 64 as illustrated in FIG. 10A or as a multilayer of non-alloyed metals as illustrated in FIG. 10B. The monolayer depicted in FIG. 10A is comprised of the metal used to form the first structural element 62 that has been deposited first, alloyed with the metal used to form the second structural element 64, which was deposited as a second step. The multilayer depicted in FIG. 10B is comprised of a layer of metal forming the first structural element 62 which is deposited as a first step, then depositing a layer of metal used to form the second structural element 64 using non-alloying materials.

FIGS. 10C and 10D illustrate transverse cross-sectional views through a second structural member 64 and a first structural member 62, respectively for all embodiments of the inventive endoluminal stent. Conventional stents typically have structural elements with generally quadrilateral transverse shapes. Typically, this is a result of using a hypotube as the starting material for stent formation. The endoluminal stents in accordance with the present invention present first and second structural elements 62, 64 which have radiused lateral surfaces 62a, 64a, respectively. In addition, each of the first and second structural elements 62, 64 also have leading and trailing surfaces which are also radiused (not shown). In this manner, all blood contact surfaces of the inventive endoluminal stent present a curvilinear surface to the blood flow thereby facilitating a more laminar blood flow over the structural elements of the inventive endoluminal stent.

An alternative embodiment of the longitudinally flexible stent of the present invention is illustrated in FIGS. 11A-11C. Like the embodiments described above, longitudinally flexible stent 100 is comprised of a plurality of first structural elements 102 and a plurality of second structural elements 104. The first structural elements 102 are positioned generally parallel to the longitudinal axis L' of the endoluminal stent 100 and are arrayed circumferentially about the circumferential axis C' of the endoluminal stents 100. The plurality of second structural elements 104 are oriented generally parallel to the circumferential axis C' of the endoluminal stent 100 and interconnect adjacent pairs of the first structural elements 102 in spaced apart relationship about the circumferential axis C' of the endoluminal stent 100. Each of the plurality of second structural elements 104 preferably has a sinusoidal configuration with at least one complete sine curve, i.e., having both positive and negative amplitude in the proximal and distal directions relative to the longitudinal axis L' of the endoluminal stent 100, being subtended between adjacent pairs of the first structural elements 102. A plurality of flex regions 110 is formed in each of the plurality of first structural members 102. Each of the plurality of flex regions 110 are formed as narrowed regions of the first structural member 102 and may be configured as V-shaped projections which project circumferentially from each of the plurality of first structural members 102. In accordance with the best mode for the present invention, it is contemplated that one of the plurality of flex regions 110 is positioned intermediate adjacent pairs of the second structural elements 104 along the first structural element 102. Alternative configurations are additionally contemplated in which the flex regions 110 are positioned between alternative pairs of second structural elements 104, are positioned only at proximal, distal or intermediate regions of the endoluminal stent, or are positioned only on selected first structural elements 102, or combinations thereof. In this manner, the longitudinal flexibility of the endoluminal stent 100 may be tailored to impart greater coefficients of longitudinal flexibility in different regions of the endoluminal stent 100.

In each of the foregoing embodiments, the, Z-axis thickness and X-Y-axis surface area of the stent first and second structural elements may be varied so as to affect the longitudinal flexibility, hoop strength and radial expansion behavior and profile of the stent. For example, a longitudinally intermediate circumferential region of the endoluminal stent may have both first and/or second structural elements which have a greater Z-axis wall thickness than proximal and distal circumferential regions of the stent. This configuration effectively reinforces the intermediate circumferential region, with the result being that the proximal and distal circumferential regions of the stent will radially dilate before the intermediate circumferential region. Alternatively, either or both of the proximal and distal circumferential regions may have first and/or second structural elements which have greater Z-axis wall thicknesses than those in a longitudinally intermediate circumferential region. This configuration will result in the longitudinally intermediate circumferential region radially dilating prior to either or both of the proximal and distal circumferential regions. Another alternative is to vary the Z-axis wall thickness of the first and/or second structural elements in a continuum along the longitudinal axis of the endoluminal stent such that the stent radially expands into a conical configuration.

Finally, in accordance with the present invention there is provided a self-supporting endoluminal graft 90 as depicted in FIG. 12. In accordance with a preferred embodiment of the invention, a graft member is formed as a discrete thin sheet or tube of biocompatible metals or metal-like material or as a laminated or plied structure of a plurality of thin sheets or tubes in adjoining relationship with one another. Like the inventive endoluminal stent, described above, the thin sheet or tube includes a plurality of first structural elements 94 that provide longitudinal or column strength to the graft, and a plurality of second structural elements 96 that provide circumferential or hoop strength to the graft. The first and second structural elements 94, 96 form integral and monolithic elements of the graft. A web 95 of the material that forms the first and second structural elements partially subtends interstitial openings 92 defined between proximate first and second structural elements 94, 96. It is preferable that the thin sheet or tube be comprised of pluralities of openings 98, which pass transversely through the web 95 of the graft member 90. The plurality of openings 98 may be random or may be patterned. It is preferable that the size of each of the plurality of openings be such as to permit cellular migration through each opening, without permitting fluid flow there through. In this manner, blood cannot flow through the plurality of openings, but various cells or proteins may freely pass through the plurality of openings to promote graft healing in vivo. The inventive self-supported endoluminal graft 90 may be fabricated of two or more discrete members each consisting of the inventive endoluminal stent described above which are concentrically engaged relative to one another, and positioned such that interstitial openings 92 in each stent member are juxtaposed adjacent a first or second structural element 94, 96 of an adjacent stent. In this manner the interstitial openings 92 of each stent 90 are at least partially occluded by the first and/or second structural elements 94, 96 of an adjacent endoluminal stent 90. Alternatively, the inventive self-supported endoluminal graft 90 may be fabricated by vacuum deposition techniques as described in co-pending, commonly assigned, U.S. patent application Ser. No. 09/443,929, filed Nov. 19, 1999, which is hereby incorporated by reference. Where the self-supported endoluminal graft is fabricated by vacuum deposition techniques, the graft may be fabricated as a laminated or plied structure in which the first and second structural elements 94, 96 of a first layer are integral and monolithic with one another, as is the web 95 which subtends the interstitial space 92 between adjacent first and second structural elements 94, 96.

With particular reference to FIG. 13 there is illustrated a laminated self-supported graft 90 in accordance with the present invention. Graft 90 is comprised of plural stent layers 90a, 90b, 90c, 90d which are successively deposited onto one another starting with first stent layer 90a. First stent layer 90a is comprised of a plurality of first structural elements 94 and second structural elements 96 (not shown), with a plurality of web regions 95, each of which subtend a space 99 defined by the first and second structural elements 94,96. At least one opening 98 is provided in at least a portion of the web regions 95. A second stent layer 90b is deposited onto the first stent layer 90a. Like the first stent layer 90a, second stent layer 90b is comprised of a plurality of first structural elements 94 (not shown) and second structural elements 96, with a plurality of web regions 95, each of which subtend a space 99 defined by the first and second structural elements 94, 96. Second stent layer 90b may be of similar geometry or different geometry than first stent layer 90a, and is positioned out-of-phase relative to the geometric pattern of first stent 90a. In being out-of-phase with first stent layer 90a, the second structural element 96 of the second stent layer 90b is adjacent and overlays both the first structural elements 94, the plurality of web regions 95 and the openings 98 in the first stent layer 90a. Successive stent layers 90c, 90d, and so forth depending upon the particular desired graft construction, are deposited upon one another such that adjacent stent layers form interlamellar endothelial growth channels 97 between successive stent layers 90a, 90b, 90c and 90d. The interlamellar endothelial growth channels 97 promote endothelialization by providing tortuous micropathways for cellular incorporation into the self-supporting graft 90.

While the present inventions have been described with reference to their preferred embodiments, those of ordinary skill in the art will understand and appreciate that a multitude of variations on the foregoing embodiments are possible and within the skill of one of ordinary skill in the vapor deposition and stent fabrication arts, and that the above-described embodiments are illustrative only and are not limiting the scope of the present invention which is limited only by the claims appended hereto.

What is claimed is:

1. An intraluminal device comprising a generally tubular member having a plurality of struts and a plurality of interconnecting members, forming circumferential walls thereof, each of the plurality of struts further having a generally sinusoidal curve thereto defining peaks and valleys of each of the plurality of struts and arranged generally sinusoidal and parallel to a longitudinal axis of the generally tubular member, each of the plurality of struts being in spaced-apart, in-phase relationship with respect to an adjacent one of the plurality of struts substantially about a circumferential aspect of the tubular member and the plurality of interconnecting members interconnecting adjacent pairs of struts and extending between a peak of a first strut and a valley of a second strut, wherein no more than one interconnecting member connects to any given peak or valley.

2. The device according to claim 1, wherein each of the struts are integral and monolithic with each of the plurality of interconnecting members.

3. The device according to claim 1, wherein the plurality of struts is discrete from and conjoined to the plurality of interconnecting members.

4. The device according to claim 1, wherein the struts and the interconnecting members are made of the same material.

5. The device according to claim 1, wherein the struts and the interconnecting members are made of different biocompatible materials.

6. The device according to claim 5, wherein the struts have material properties different and distinct from the interconnecting members.

7. The device according to claim 1, wherein the struts and the interconnecting members further comprise luminal surfaces thereof having controlled heterogeneities thereupon.

8. The device according to claim 7, wherein the controlled heterogeneities are selected from the group consisting of grain size, grain phase, grain material composition, stent material composition and surface topography.

9. The device according to claim 7, wherein the controlled heterogeneities define polar and non-polar binding sites for binding blood plasma proteins.

10. The device according to claim 7, wherein the controlled heterogeneities are dimensioned to have a blood contact surface area substantially similar in size as endothelial cell surface integrin clusters.

11. The device according to claim 1, wherein the struts and the interconnecting members are made of materials selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof, and stainless steel.

12. An intraluminal stent comprising a generally tubular member having a plurality of generally sinusoidal members being substantially parallel to a longitudinal axis of the generally tubular member and extending along the entire length of the longitudinal axis, each of the plurality of generally sinusoidal members being in spaced-apart, in-phase relationship with respect to an adjacent one of the plurality of generally sinusoidal members substantially about a circumferential aspect of the tubular member; and a plurality of interconnecting members interconnecting adjacent pairs of the generally sinusoidal members and extending between a peak of a first generally sinusoidal member and a valley of a second, circumferentially adjacent generally sinusoidal member, such that no more than one interconnecting member connects to any given peak or valley of adjacent generally sinusoidal members.

* * * * *